(12) United States Patent
Conklin et al.

(10) Patent No.: US 12,029,651 B2
(45) Date of Patent: Jul. 9, 2024

(54) IMPLANT HOLDER ASSEMBLY WITH ACTUATOR FOR HEART VALVE REPAIR AND REPLACEMENT

(71) Applicant: Edwards Lifesciences Corporation, Irvine, CA (US)

(72) Inventors: Brian S. Conklin, Orange, CA (US); Louis A. Campbell, Santa Ana, CA (US); Derrick Johnson, Orange, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 693 days.

(21) Appl. No.: 17/244,435

(22) Filed: Apr. 29, 2021

(65) Prior Publication Data
US 2021/0259841 A1 Aug. 26, 2021

Related U.S. Application Data

(63) Continuation of application No. PCT/US2019/058638, filed on Oct. 29, 2019.

(60) Provisional application No. 62/754,066, filed on Nov. 1, 2018.

(51) Int. Cl.
*A61F 2/24* (2006.01)

(52) U.S. Cl.
CPC .......... *A61F 2/2496* (2013.01); *A61F 2/2412* (2013.01); *A61F 2/2427* (2013.01); *A61F 2/2445* (2013.01); *A61F 2/2466* (2013.01)

(58) Field of Classification Search
CPC .... A61F 2/2496; A61F 2/2412; A61F 2/2427; A61F 2/2445; A61F 2/2466
See application file for complete search history.

(56) References Cited

U.S. PATENT DOCUMENTS

| | | | |
|---|---|---|---|
| 2009/0093877 A1* | 4/2009 | Keidar | A61F 2/2427 623/2.11 |
| 2018/0116795 A1* | 5/2018 | Conklin | A61F 2/2427 |

* cited by examiner

*Primary Examiner* — Suba Ganesan
(74) *Attorney, Agent, or Firm* — Guy Cumberbatch

(57) ABSTRACT

An articulating implant holder system for heart valve repair or replacement has an implant configured to be secured to a heart valve annulus, an implant holder secured to the implant, an articulating handle assembly comprising a handle, a swivel pivotably secured to the handle at a first location and a connector pivotably secured to the swivel at a second location, an actuating cable secured between the handle and the connector to cause the swivel to move from a first position to a second position, and a latch removably secured to the implant holder. A plurality of sizer heads are configured to correspond to different sizes of heart valve annuluses and each of the plurality of sizer heads has a latching feature. A latching feature of the swivel is configured to removably snap on to the latching feature of each of the plurality of sizer heads and is configured to permanently snap on to the latch.

20 Claims, 28 Drawing Sheets

IMPLANT HOLDER ASSEMBLY WITH ACTUATOR FOR HEART VALVE REPAIR AND REPLACEMENT

CROSS REFERENCE TO RELATED APPLICATIONS

This application is a continuation of International Application No. PCT/US2019/058638, filed Oct. 29, 2019, which claims the benefit of U.S. Application No. 62/754,066, filed Nov. 1, 2018, the entire contents all of which are incorporated by reference for all purposes.

This application is related to U.S. Application No. 62/754,091, filed Nov. 1, 2018, and to U.S. Application No. 62/754,070, filed Nov. 1, 2018, the entire disclosures all of which are incorporated by reference for all purposes.

FIELD

The present disclosure relates generally to medical devices and to tools for delivering such medical devices. More specifically, the disclosure relates to the surgical repair and replacement of native heart valves that have malformations or dysfunctions with prosthetic heart valves or annuloplasty rings that can be implanted through a minimally sized incision. Embodiments of the invention relate to holders for facilitating the implantation of a prosthetic heart valve or annuloplasty ring at a native valve annulus, holders for related sizer heads, and methods of using the holders to facilitate implantation of such valves and rings.

BACKGROUND

Referring first to FIG. 1, the human heart is generally separated into four pumping chambers which pump blood through the body. Each chamber is provided with its own one-way exit valve. The left atrium receives oxygenated blood from the lungs and advances the oxygenated blood to the left ventricle through the mitral (or bicuspid) valve. The left ventricle collects the oxygenated blood from the left atrium and pushes it through the aortic valve to the aorta, where the oxygenated blood is then distributed to the rest of the body. Deoxygenated blood from the body is then collected at the right atrium and advanced to the right ventricle through the tricuspid valve. The right ventricle then advances the deoxygenated blood through the pulmonary valve and the pulmonary arteries to the lungs to again supply the blood with oxygen.

Each of the valves associated with the chambers of the heart are one-way valves that have leaflets to control the directional flow of the blood through the heart and to prevent backflow of the blood into other chambers or blood vessels that are upstream of the particular chamber. The valves are each supported by an annulus having a dense fibrous ring attached either directly or indirectly to the atrial or ventricular muscle fibers.

When a valve becomes diseased or damaged, the efficiency and/or general functionality of the heart may be compromised. Diseased heart valves may be categorized as either stenotic, wherein the valve does not open sufficiently to allow adequate forward flow of blood through the valve, and/or incompetent, wherein the valve does not close completely, causing excessive backward flow of blood through the valve when the valve is closed. Valve disease can be severely debilitating and even fatal if left untreated.

Various surgical techniques can be performed to replace a diseased or damaged valve. For example, the leaflets of a diseased or damaged native valve may be at least partially removed to prepare the valve annulus for receiving a prosthetic replacement valve. FIG. 2 shows an example of one type of popular prosthetic replacement valve 1 that is a tissue-type bioprosthetic valve generally constructed with natural-tissue valve leaflets 2, made for example, from porcine tissue or bovine pericardium, or from synthetic or semisynthetic material, that are mounted on a surrounding valve stent structure or frame 3. The shape and structure of the leaflets 2 are supported by a number of commissure posts 4 positioned circumferentially around the valve stent structure 3. In these valves, a biocompatible cloth-covered suture or sewing ring 5 can also be provided on an inflow end of the stent structure 3 of the valve 1, to facilitate easier attachment to the native valve annulus. Such prosthetic valves function much like natural human heart valves, where the leaflets coapt against one another to effect the one-way flow of blood.

When implanting a tissue type prosthetic valve as described above at a native valve annulus, a number of sutures may be involved in the attachment process, many of which may be pre-installed for providing a track on which the valve is advanced, or "parachuted," until it is properly positioned at the implant site. Additional sutures may also be applied between the prosthetic valve and the heart walls after proper placement, to securely attach or hold the valve implant in place.

In addition, depending on the direction of implantation, for example with some mitral valve replacement procedures, commissure posts of the stent or frame, or other portions of the prosthetic valve, may be pointed distally and advanced on a blind side of the valve, thereby obstructing visibility of the posts or other portions during advancement and implantation. Such procedures can also require a prosthetic valve and its holder to fit through an incision of approximately 15-20 mm in its narrowest direction or dimension. Meanwhile, in some cases, the prosthetic valves are implanted through small access channels using one of various minimally invasive surgical procedures, where visibility at the implant site may be impeded or obstructed.

Each of the above factors may lead to tangling of the sutures with the valve prosthesis, most commonly with the commissure posts of the frame, since the commissure posts provide a protrusion on which the sutures can easily loop around and tangle. This type of entanglement of sutures with prosthetic valves is referred to as "suture looping," which specifically refers to instances where a suture is inadvertently wrapped around one or more of the commissure post tips, where it can then migrate towards and damage the leaflets or interfere with proper leaflet coaptation or other valve operation when the sutures are tightened or secured, resulting in improper valve operation.

Examples of replacement valve implant procedures are described in more detail in U.S. Patent Application Publication No. 2018/0116795 A1, the contents of which are incorporated herein by reference in their entirety. In the referenced publication, a prosthetic heart valve and valve holder are pre-attached to a handle that allows tilting of the valve holder from a switch on the handle. This concept is very amenable to minimally invasive surgery procedures as the valve can be collapsed and then tilted on the end of the handle to achieve a very low profile that allows insertion between a patient's ribs in a non-rib spreading thoracotomy.

Because a holder is employed to hold the valve during the implanting step, it becomes necessary at some point to separate the implanted valve from the valve holder. Such procedures, however, require space for additional instruments at the implant site. Therefore, it is desired to find a simple way to release the holder and remove it from the valve.

Valve implant procedures also need to account for proper sizing of the valve annulus. Accordingly, the surgeon is often provided with a tray of sizer heads having external shapes and sizes similar to those of valves to be implanted. In each tray, the sizer heads have barrels of different sizes and the one that best fits the native valve annulus is used to select the proper prosthetic valve. Present methods of sizing a valve annulus, however, are inefficient and awkward to employ due to the need to use additional instruments during the sizing procedure. This is especially true for procedures to size an annulus or deliver an implant through a minimally sized incision. In view of the above, it would be desirable to have a modular system that uses the same handle with tilting mechanism for both sizing and valve implantation. This would give the surgeon an efficient process for both sizing and implanting the valve through a very minimally sized incision, such as during a non-rib-spreading thoracotomy.

Another surgical procedure for treating defective valves is through repair or reconstruction of the diseased or damaged valve. One repair technique that has been shown to be effective in treating incompetence is annuloplasty, in which the effective size and/or shape of the valve annulus is modified by securing a repair segment, such as an annuloplasty ring, around all or a portion of the heart valve annulus. For example, the valve annulus may be contracted by attaching a prosthetic annuloplasty ring to an interior wall of the heart around the valve annulus. The annuloplasty ring is designed to support the functional changes that occur during the cardiac cycle, maintaining coaptation and valve integrity to prevent reverse flow while permitting good hemodynamics during forward flow.

The annuloplasty ring typically comprises an inner substrate, often formed from a metal (such as stainless steel or titanium) or from a flexible material (such as silicone rubber or Dacron cordage), which is typically covered with a biocompatible fabric or cloth, forming a sewing cuff, to allow the ring to be sutured to the heart tissue. Annuloplasty rings include annuloplasty bands and may be stiff or flexible, may be split (including rings that extend at least halfway around the valve annulus) or continuous, and may have a variety of shapes, including circular, D-shaped, C-shaped, saddle-shaped, and/or kidney-shaped. Examples are seen in U.S. Pat. Nos. 5,041,130, 5,104,407, 5,201,880, 5,258,021, 5,607,471, 6,187,040, and 6,805,710, the contents of which are incorporated herein by reference in their entirety.

In the usual mitral annuloplasty ring implant procedure, an array of separate implant sutures are first looped through all or portions of the exposed mitral annulus at intervals spaced equidistant from one another, such as for example 4 mm intervals. The surgeon then threads the implant sutures through the annuloplasty ring at more closely spaced intervals, such as for example 2 mm. This occurs with the prosthesis outside the body, typically secured to a peripheral edge portion of a holder or template. The ring on the holder is then advanced (parachuted) distally along the array of pre-anchored implant sutures into contact with the valve annulus, thus effecting a reduction in valve annulus circumference. At this point a handle used to manipulate the holder or template may be detached for greater visibility of the surgical field. The surgeon ties off the implant sutures on the proximal side of the ring, and releases the ring from the holder or template, typically by severing connecting sutures at a series of cutting guides. Examples of annuloplasty ring implant procedures are described in U.S. Pat. Nos. 8,216, 304 and 8,152,844, the contents of which are incorporated herein by reference in their entirety.

Implanting an annuloplasty ring may be achieved using minimally invasive procedures. Using a standard atriotomy approach to the mitral valve for repair, however, does not generally achieve straight-on access to the mitral valve annulus. Instead, the surgeon often sees and accesses the valve from an angle. Therefore, when the sutures are placed in the annuloplasty ring and it is parachuted to the annulus, the ring and holder must be reoriented to sit flat against the annulus. In addition, the annuloplasty ring must be passed through a relatively small port into the chest. This can be complicated by the bulk of some holders, so in some instances a surgeon simply removes the holder from the ring prior to parachuting the ring down the sutures and onto the valve annulus. The removal of the entire holder from the ring, however, can make control of the annuloplasty ring more difficult.

In addition, current annuloplasty rings have holder systems that utilize a snap-in feature to lock their handles into the holders at a fixed angle. While the use of snap-in features may be convenient for initially attaching the handles to the holders, it may be difficult to separate the handle during implantation, especially if the prosthesis is already parachuted to the annulus. Furthermore, removing the holder prematurely may not be desirable in the case of a very flexible implant, since the holder maintains the shape of the implant while knots are being tied affixing the implant to the annulus.

Additionally, the angle at which the handles are attached to the implant holders may not be optimal for all procedural approaches. For example, the optimum angle between the handle shaft and the implant for a full sternotomy may be completely different than for a minimally invasive thoracotomy. Likewise, with the implant at a fixed angle relative to the handle, it may be difficult to insert the implant through a minimally-sized incision.

Given the above, it would be desirable to have a holder system for an annuloplasty procedure or a valve replacement procedure that would allow for articulation of the implant from the handle, yet be easily detached from the holder. Furthermore, a modular system is desired where sizer heads for the annuloplasty ring or prosthetic valve can be attached to the articulating handle, followed by the actual implant.

SUMMARY

In a preferred embodiment of the present invention, an articulating implant holder system for heart valve repair or replacement includes an implant configured to be secured to a heart valve annulus, and an implant holder having a bottom portion and a top portion. The system further includes an articulating handle assembly having a handle and a swivel, the swivel having a latching feature and the handle pivotably secured to the swivel at a first location. The handle assembly further includes a connector pivotably secured to the swivel at a second location. An actuating cable secured between the handle and the connector causes the swivel to move from a first position to a second position. A latch is removably secured to the implant holder. A plurality of sizer heads are included that correspond to different sizes of heart valve annuluses. Each of the plurality of sizer heads has a latching feature and the latching feature of the swivel is configured to removably snap on to the latching feature of each of the plurality of sizer heads. The latching feature of the swivel is also configured to permanently snap on to the latch.

In a further embodiment, the latching feature of each of the plurality of sizer heads comprises a ramp that is configured to engage the latching feature of the swivel to secure the articulating handle assembly to the sizer head and to permit removal of the articulating handle assembly from the sizer head. Each of the plurality of sizer heads may also have a recessed portion to receive the swivel from the top before the latching feature of the swivel engages the ramp.

In a preferred embodiment, the implant is a heart valve prosthesis and each of the plurality of sizer heads has a cylinder-like portion extending down from a top portion. Each sizer head of the plurality of sizer heads can also be a monolithic piece.

In a further embodiment, the latch is secured to the top portion of the implant holder by a release suture that is accessible to cutting from above by a surgeon. The latch is further secured by a retention tab located in a retention opening of the implant holder. The latch may further have a recessed portion and the swivel can be configured to enter the recessed portion from the top and then slide to a side to permanently snap the latching feature of the swivel on to the latch.

In an alternative embodiment, the implant is a heart valve prosthesis and the implant holder comprises a rotor secured to the heart valve by sutures to move leaflets of the heart valve from a first position where the leaflets of the heart valve are apart to a second position where the leaflets are closer together. An activator to engage and turn the rotor from the first position to the second position may be employed. Preferably, the latch has a through opening to permit the activator to pass there through to engage the rotor.

In another preferred embodiment, the latching feature of the swivel comprises two flexible arms that extend away from a base of the swivel, wherein the base of the swivel is supported by the latch when assembled together. A free end of each of the two flexible arms includes a wall to engage corresponding walls of the latch to prevent the swivel from being removed from the latch.

In an alternative embodiment, the implant is an annuloplasty ring. For example, the articulating implant holder system for heart valve repair includes an annuloplasty ring configured to be secured to a heart valve annulus and an implant holder having a bottom portion and a top portion. The annuloplasty ring is secured to the bottom portion of the implant holder. An articulating handle assembly includes a handle and a swivel and the swivel has a latching feature. The handle is pivotably secured to the swivel at a first location. A connector is pivotably secured to the swivel at a second location and an actuating cable is secured between the handle and the connector to cause the swivel to move from a first position to a second position. A latch is removably secured to the top portion of the implant holder by a release suture that is accessible to cutting from above by a surgeon. In addition, the latching feature of the swivel is configured to permanently snap on to the latch.

In a further embodiment, an articulating implant holder system for heart valve repair includes an annuloplasty ring configured to be secured to a heart valve annulus and an implant holder having a bottom portion and a top portion. An articulating handle assembly includes a handle and a swivel and the swivel has a latching feature. The handle is pivotably secured to a swivel at a first location. A connector is pivotably secured to the swivel at a second location and an actuating cable is secured between the handle and the connector to move the swivel from a first position to a second position. The articulating handle assembly is mounted on the top portion of the implant holder and is secured by a suture. The suture is threaded across a suture mount of the swivel that forms a single cutting point gap, down through the implant holder, and back up through the implant holder to a base of the swivel opposite the suture mount to secure the swivel to the implant holder and to permit release of the articulating handle assembly from the implant holder at a single cutting point at the suture mount.

Other embodiments provide a method for delivering and implanting an annuloplasty ring or heart valve in a patient in need thereof using a holder or implant-holder system disclosed herein.

BRIEF DESCRIPTION OF THE DRAWINGS

Further features and advantages of the invention will become apparent from the description of embodiments using the accompanying drawings. In the drawings.

DETAILED DESCRIPTION

Disclosed herein are various implant holder assemblies for assisting in the delivery and implantation of a prosthetic heart valve or an annuloplasty ring at an implant site, and methods of using those holder assemblies. Embodiments of the invention include a modular sizer and valve system using the same handle with articulating tip for both sizing and valve implantation. Another embodiment of the invention includes a holder for an annuloplasty ring that can be articulated by the handle and wherein the handle can be easily detached from the ring holder. In a further embodiment, a modular system is provided where the articulating handle can be attached to different sizer heads, then detached and attached to an annuloplasty ring holder.

Figure 1:
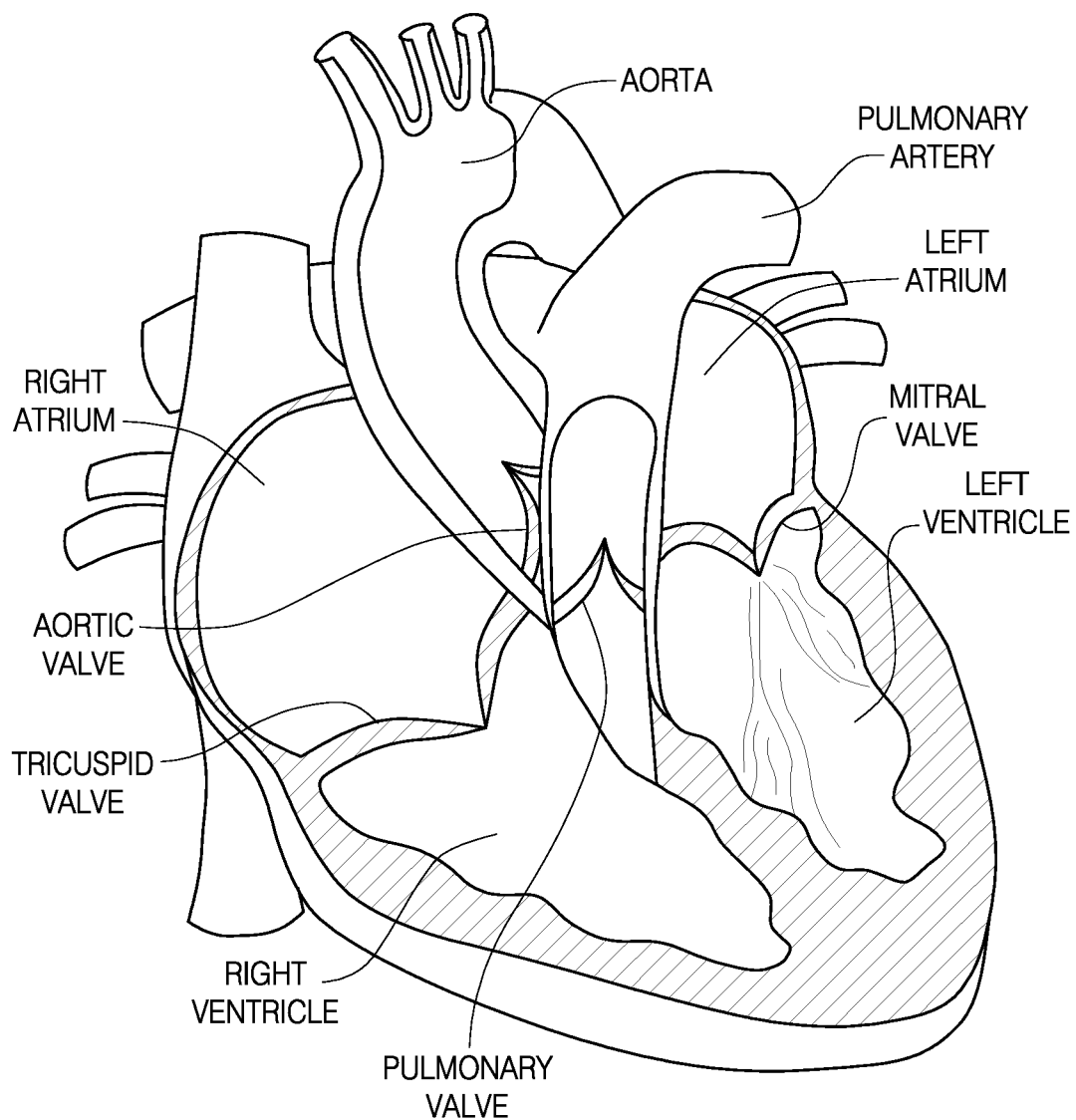
FIG. 1 shows a schematic cross-sectional view of a human heart.
Figure 2:
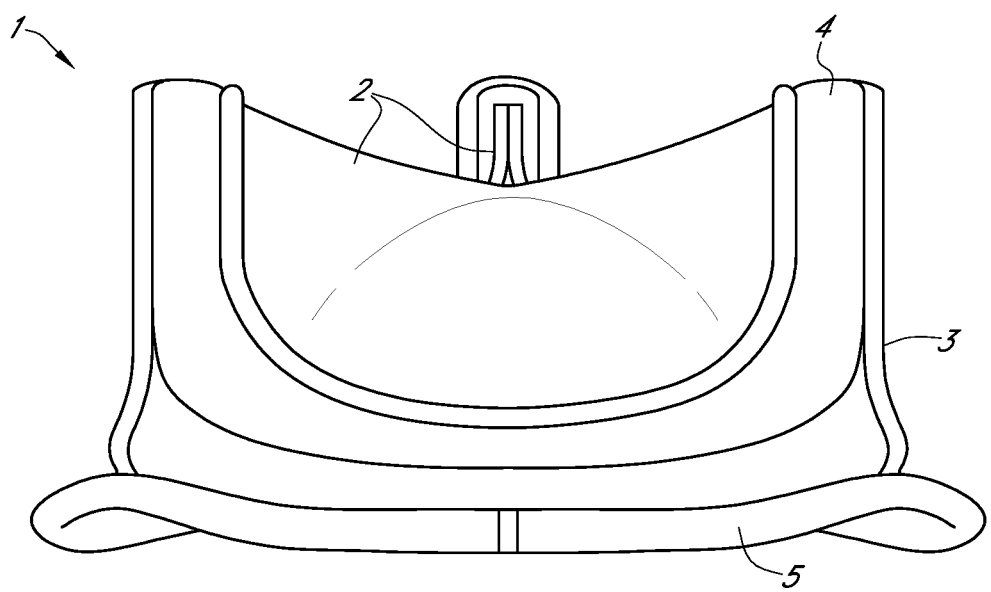
FIG. 2 shows a schematic perspective view of an example of a prosthetic valve that can be used with embodiments of the invention.
Figure 3:
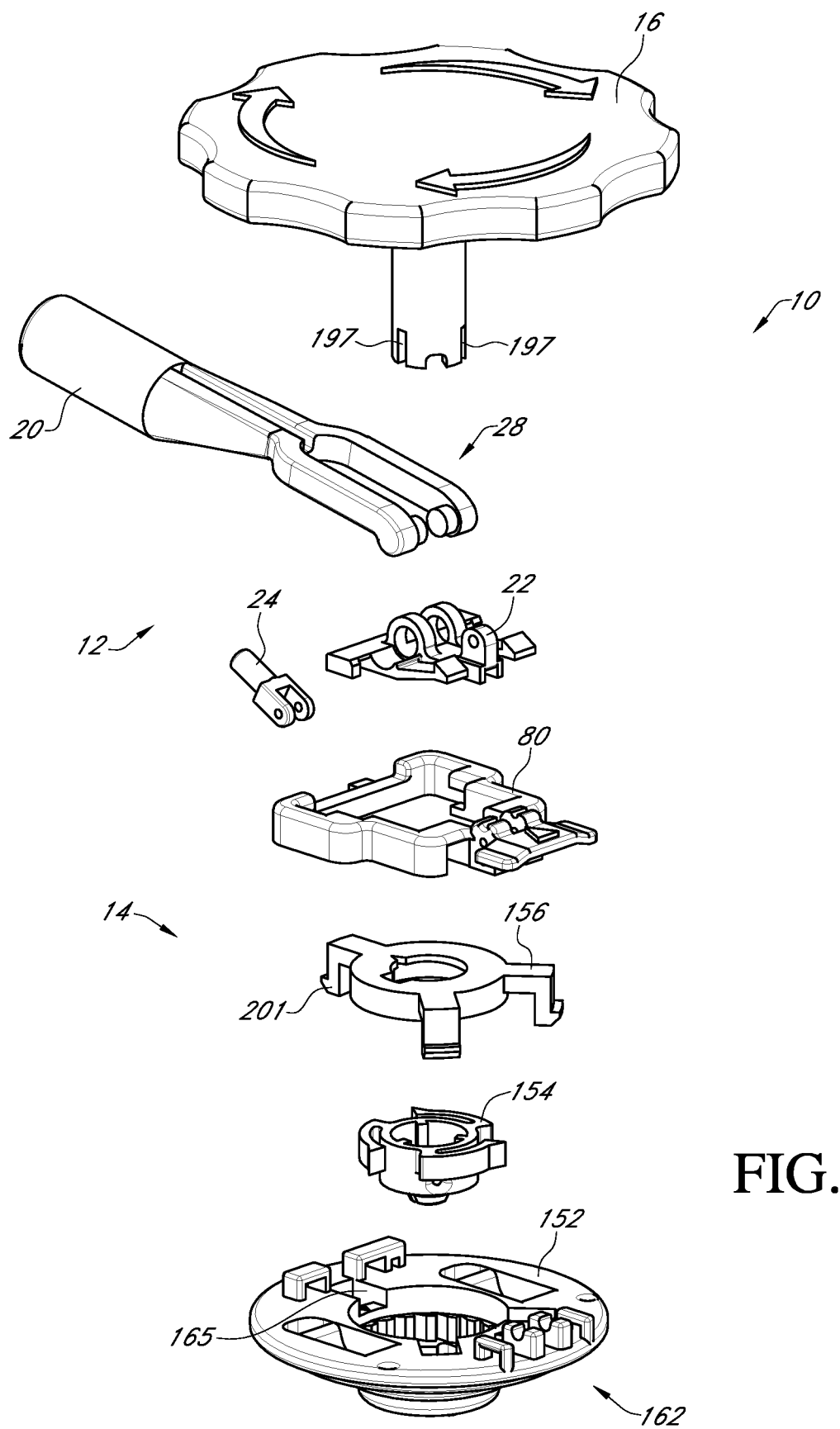
FIG. 3 shows an exploded perspective view of a heart valve implant holder assembly according to an embodiment of the invention.
Figure 4A:
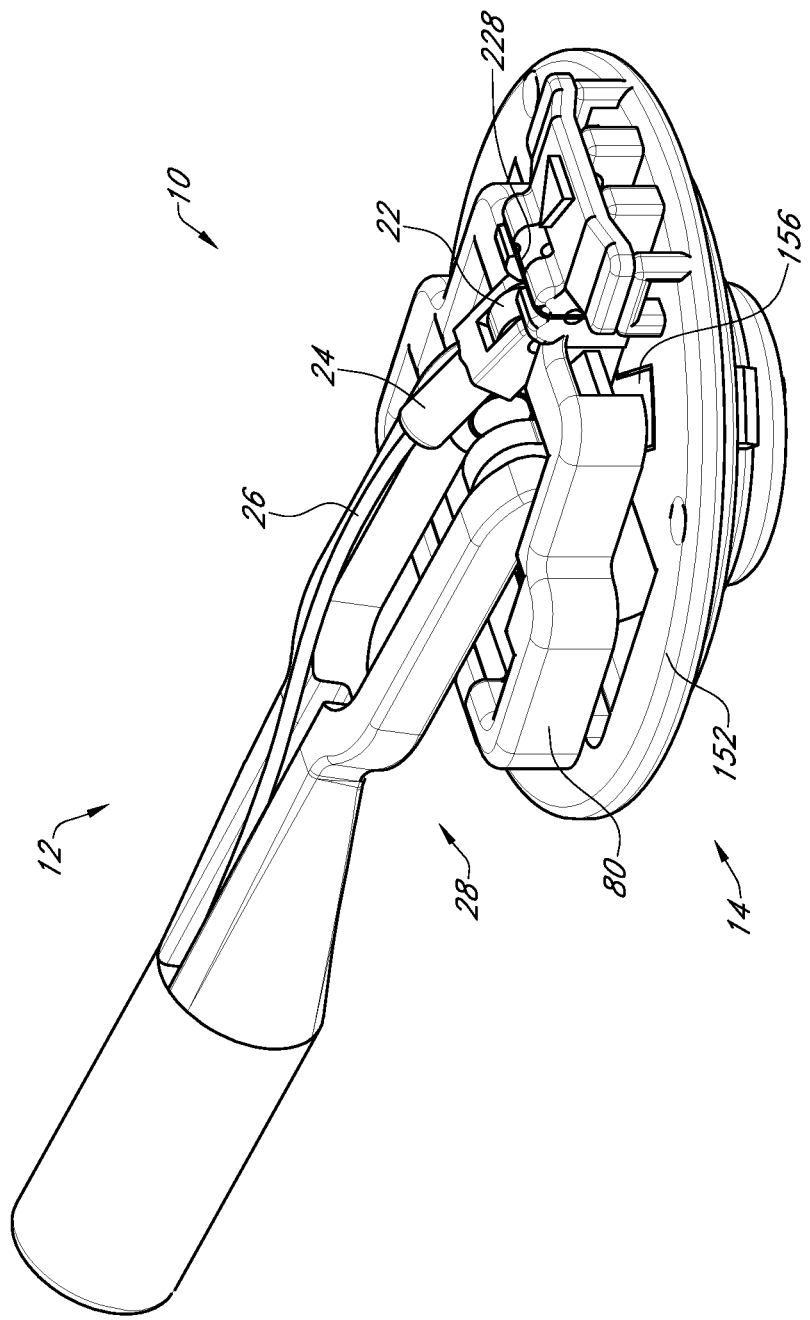
FIG. 4A shows a perspective view of the heart valve implant holder assembly of FIG. 3 (without the activator dial) in a low profile orientation.
Figure 4B:
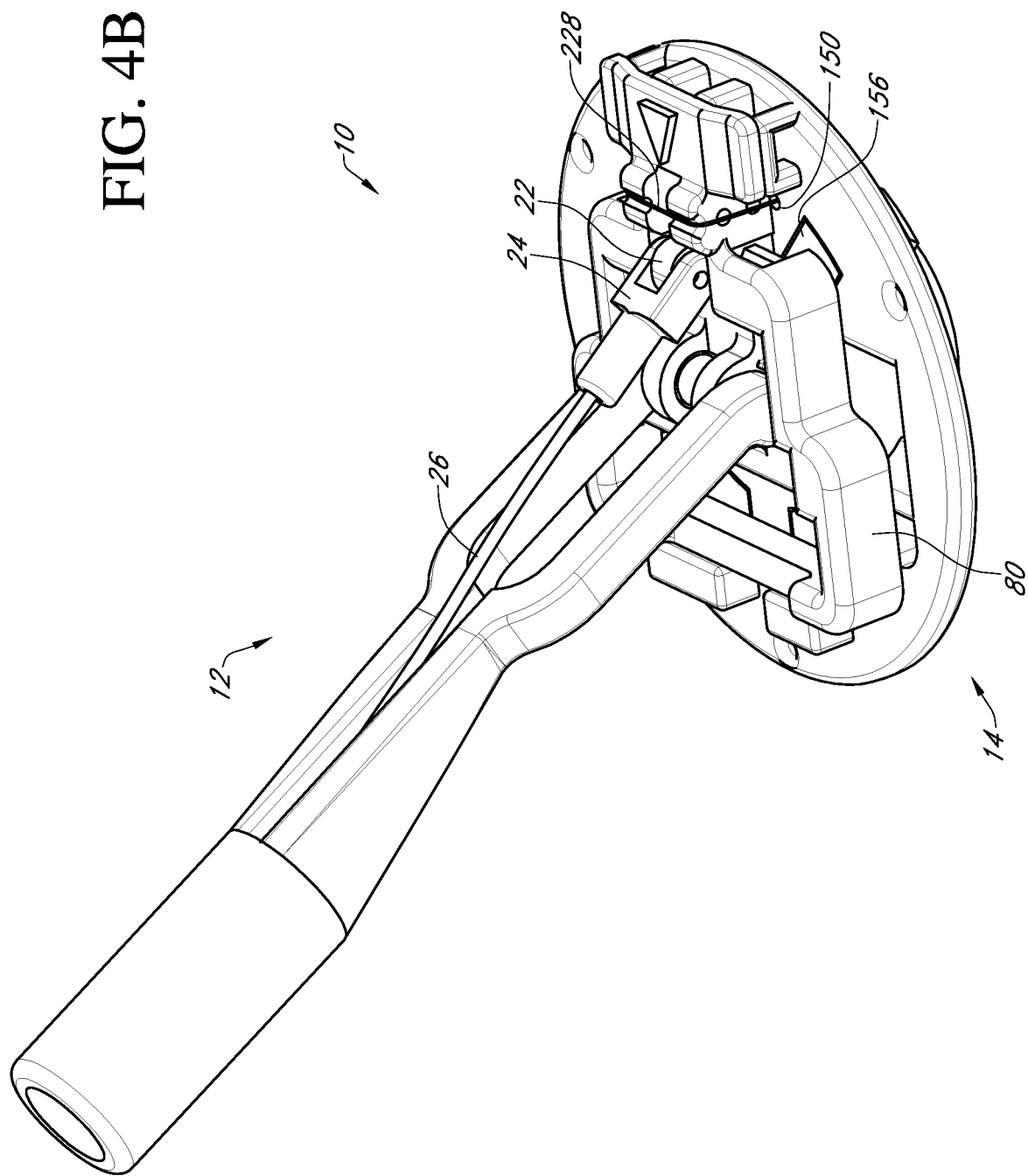
FIG. 4B shows a perspective view of the heart valve implant holder assembly of FIG. 4A in a second orientation.
Figure 5:
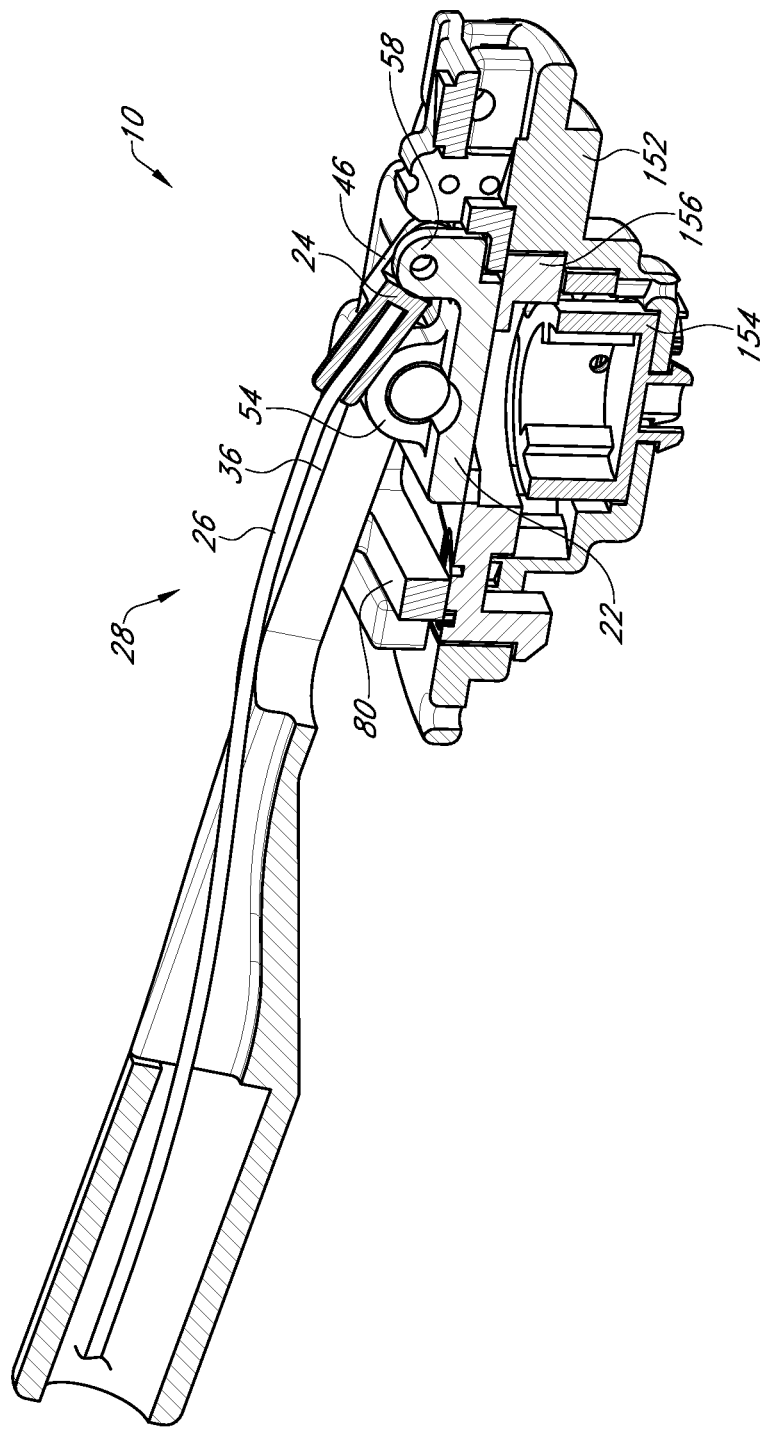
FIG. 5 shows a cross-sectional view of the heart valve implant holder assembly of FIG. 4A.
Figure 16:
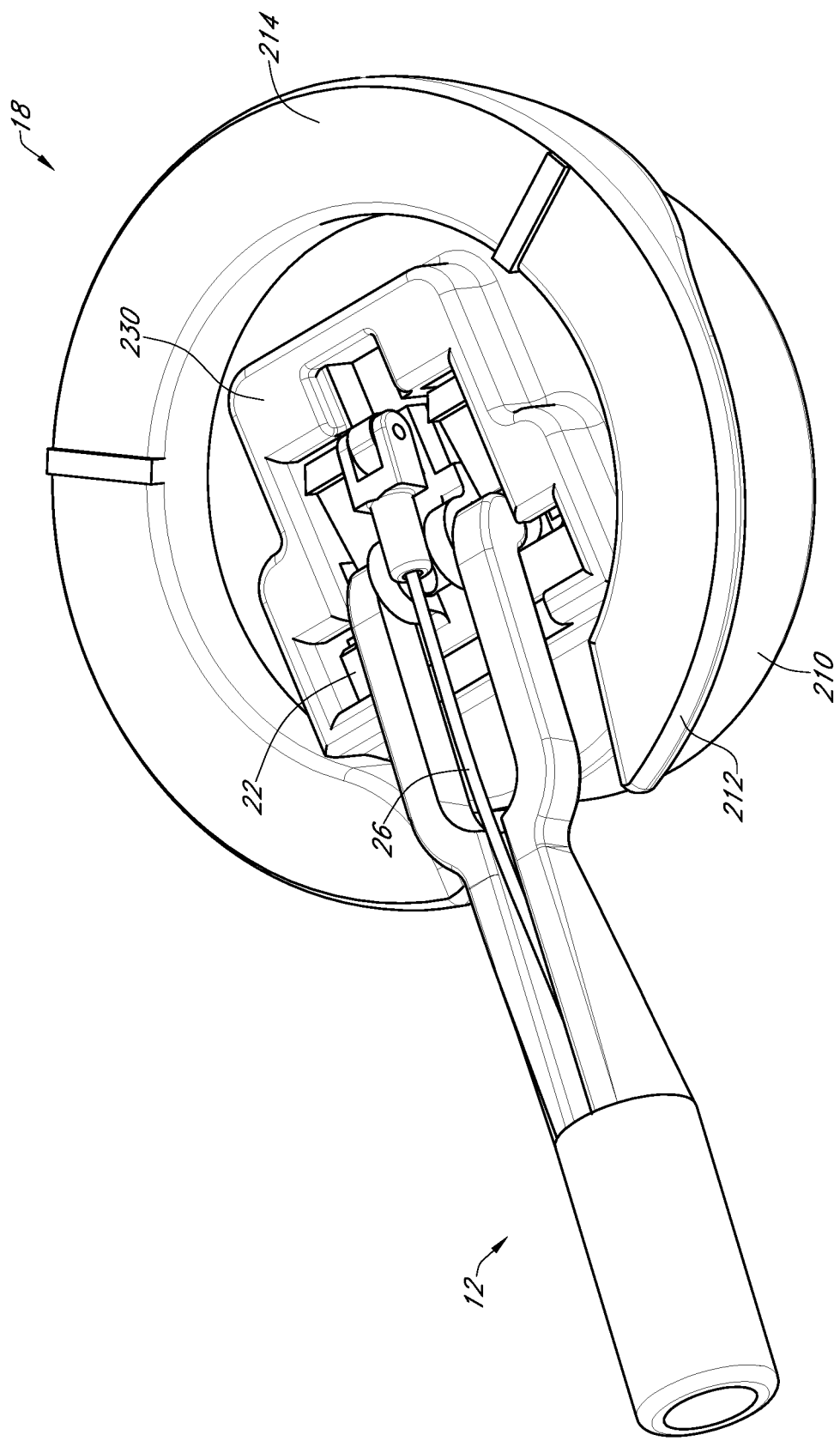
FIG. 16 shows the sizer head of FIG. 15 and the handle attachment of the heart valve implant holder assembly of FIG. 3 in a pre-assembled state.
Figure 17:
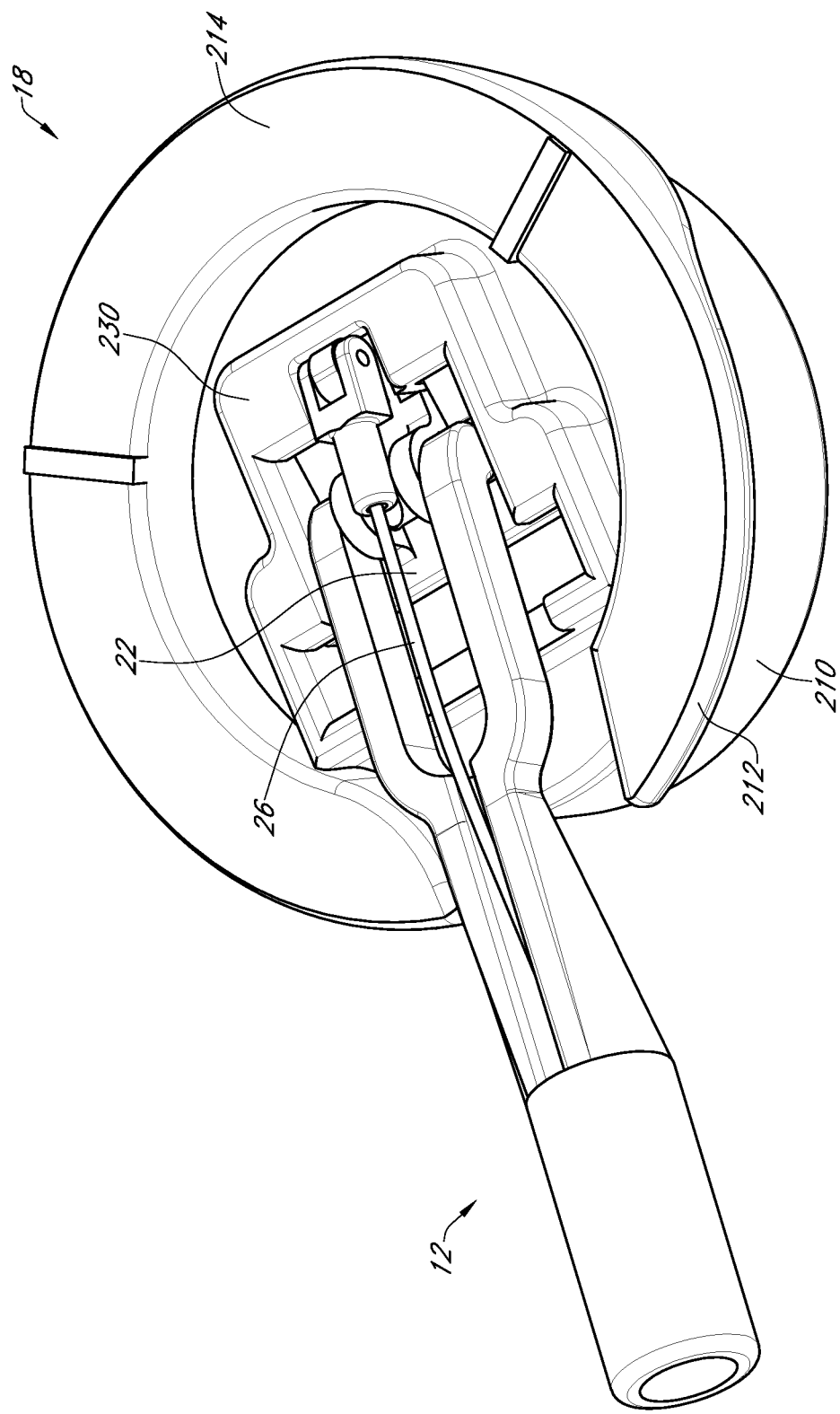
FIG. 17 shows the sizer head of FIG. 15 and the handle attachment of the heart valve implant holder assembly of FIG. 3 in the assembled state.

With reference to FIGS. 3-5, a heart valve implant holder assembly 10 includes a handle assembly 12, a valve latch 80, a valve holder 14, an activator dial (or actuator) 16, and a set of sizer heads 18 (one shown in FIG. 16). A sewing ring 5 of a prosthetic heart valve 1 (FIG. 2) is attached to the bottom of the valve holder 14. The handle assembly 12 includes a handle 20 connected to a rotatable swivel 22. A clevis (or connector) 24 and a malleable shaft 26 (FIG. 4A) also connect the handle to the swivel 22. The swivel 22 rotates at a distal end 28 of the handle and is actuated by the shaft 26 through a toggle or thumb knob (not shown) on a proximal end of the handle. The malleable shaft can be a wire and is preferably made of a suitable material to actuate the swivel, yet flexible enough to permit a suitable range of motion of the swivel during actuation.

Figure 6:
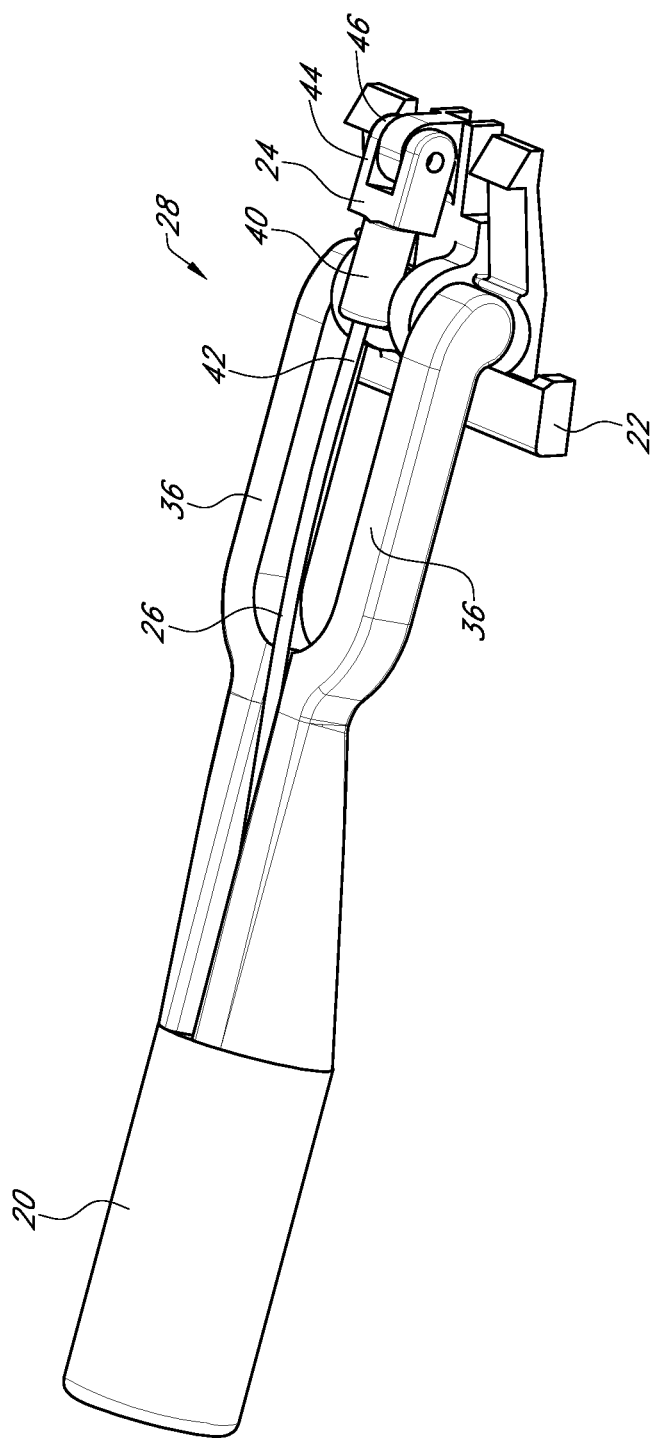
FIG. 6 shows a perspective view of a handle assembly of the heart valve implant holder assembly of FIG. 3.

With reference to FIG. 6, the distal end 28 of the handle forms a pair of arms 36. The clevis 24 has a proximal shaft 40 to receive and hold a distal end 42 of the shaft 26. A distal end 44 of the clevis also forms a pair of arms 46. The arms 36 of the handle and the arms 46 of the clevis are pivotally attached to the swivel 22 to actuate the swivel and move the valve and the valve holder 14 from a low profile orientation shown in FIG. 4A (permitting easier insertion of the valve and valve holder into the patient's body) to a different orientation that is better suited for securing the valve to the native valve annulus shown in FIG. 4B.

Figure 7A:
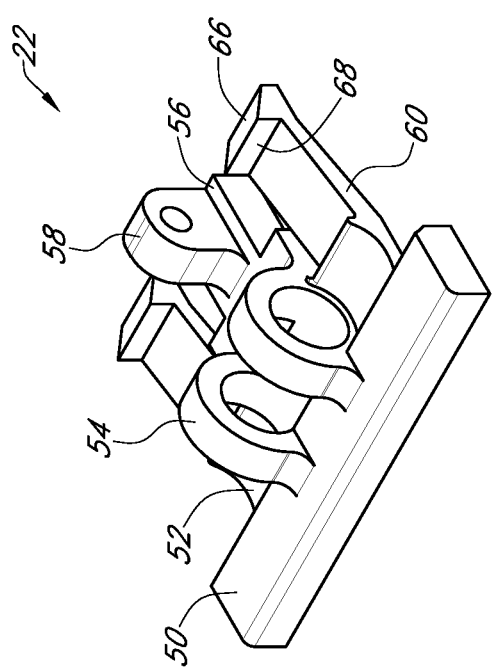
FIG. 7A shows a top perspective view of a swivel of the handle assembly of FIG. 6.
Figure 7B:
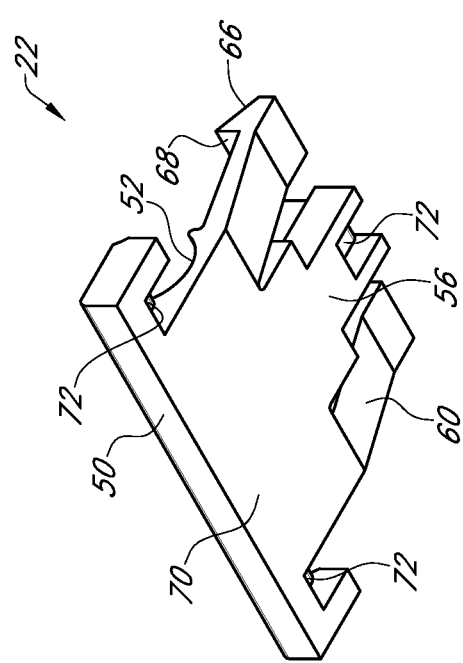
FIG. 7B shows a bottom perspective view of the swivel of the handle assembly of FIG. 6.

With reference to FIGS. 7A and 7B, the swivel 22 has a base 50, an extension 52 from the base that has connecting ears 54 and a central stub 56 that projects from the extension 52 away from the base 50. The central stub 56 supports a central bearing 58. Flexible latches 60 also project from the extension 52 along each side of and spaced from the central stub 56. The connecting ears 54 and the central bearing 58 have openings or through holes to facilitate a rotatable connection with the handle arms 36 and the clevis arms 46, respectively (FIG. 5). The rotatable connection can be achieved by pins, a snap-on connection or other suitable means.

Each of the flexible latches 60 is angled slightly upward from the plane of the base 50 and at its distal end forms a ramp 66 and a retention wall 68 for attachment to the valve latch 80 as will be described later. A bottom 70 of the swivel 22 forms three recesses 72. Two of the recesses are located at opposite ends of the base extension 52 and the third recess is located under the central bearing 58 of the swivel. The recesses are intended to receive retention tabs 94 on the valve latch 80 of the valve holder 14 (see FIG. 8B).

Figure 8A:
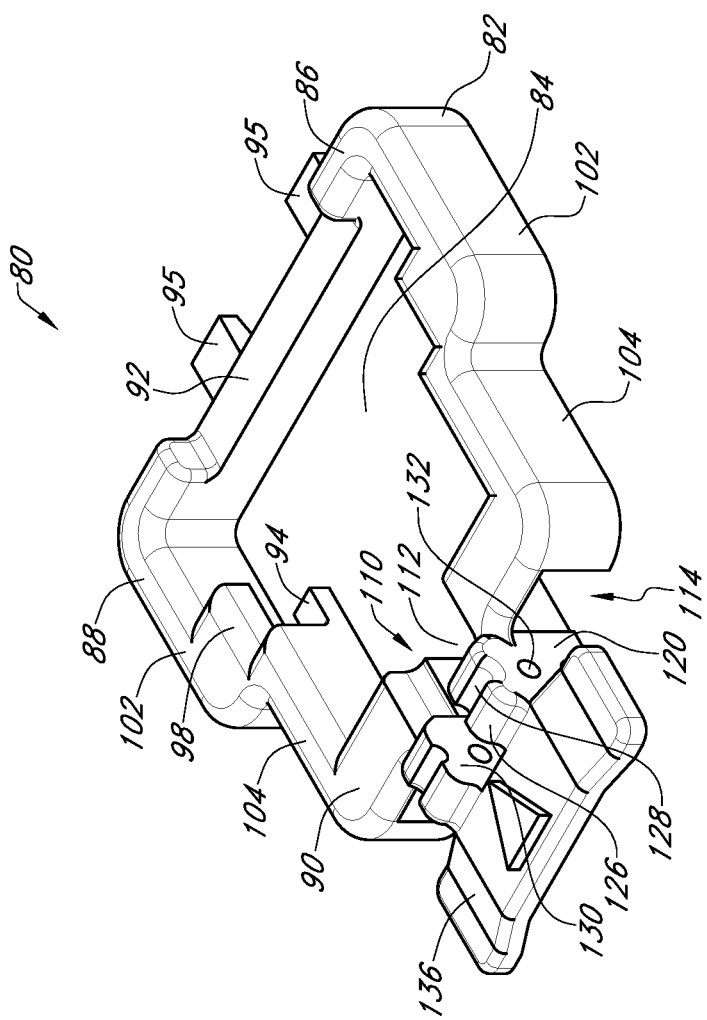
FIG. 8A shows a top perspective view of a valve latch of the heart valve implant holder assembly of FIG. 3.
Figure 8B:
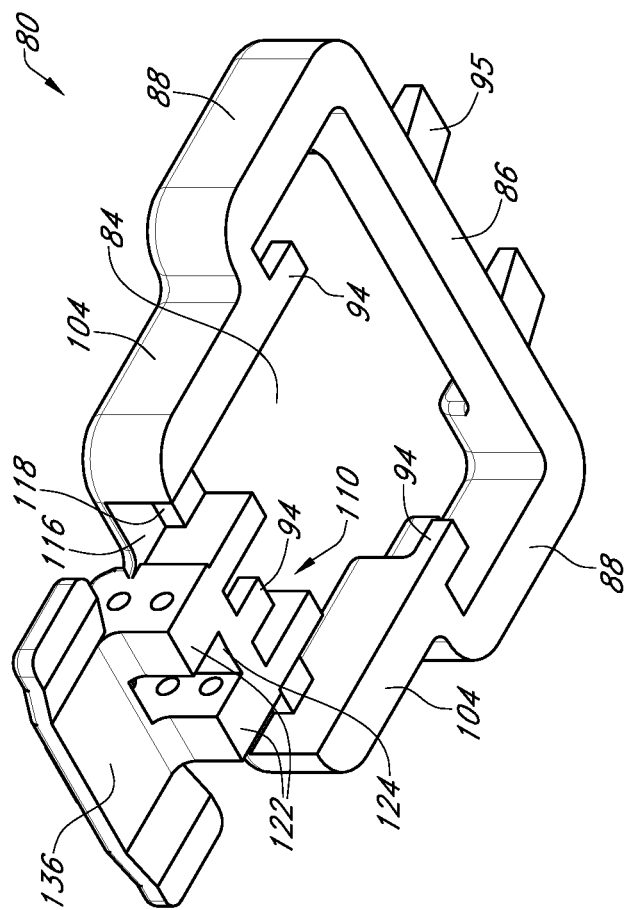
FIG. 8B shows a bottom perspective view of the valve latch of the heart valve implant holder assembly of FIG. 3.

With reference to FIGS. 8A and 8B, the valve latch 80 has a frame 82 with an opening 84 extending there through. The frame 82 has a back wall 86, two side walls 88 and a front wall 90. The back wall 86 has an upper recessed portion 92 that provides clearance for the handle 20 when the handle assembly is attached to the valve holder. The back wall 86 also has a pair of retention teeth 95 extending from the back wall in a direction away from the front wall 90.

Figure 14:
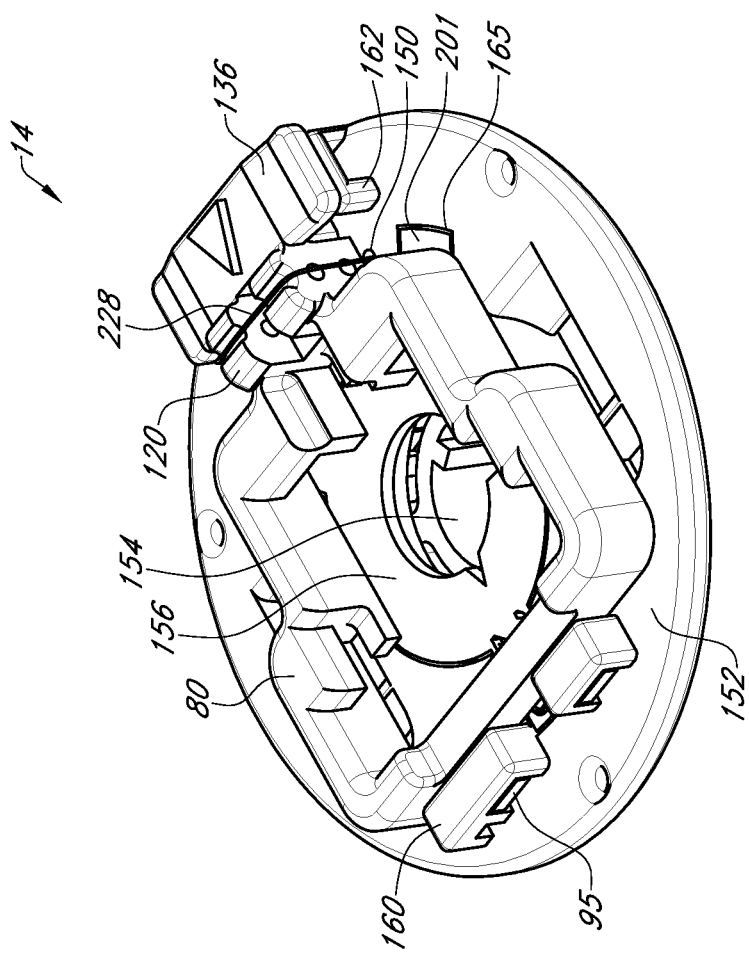
FIG. 14 shows a perspective view of the valve latch and the valve holder of the heart valve implant holder assembly of FIG. 3 in the assembled state.
Figure 15:
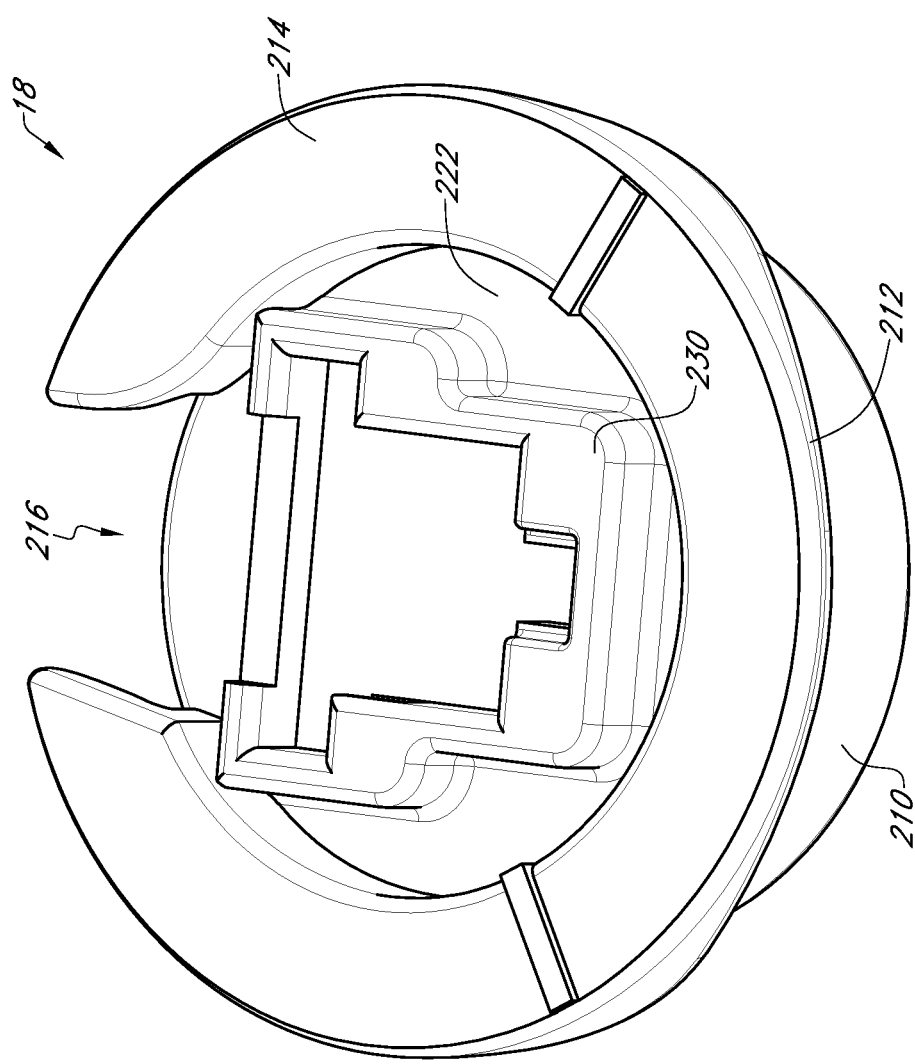
FIG. 15 shows a perspective view of a sizer head according to an embodiment of the present invention.

The side walls 88 are symmetrical to each other and have a shape to reduce interference with access features of a body 152 of the valve holder 14 (see FIG. 14). First segments 102 of the side walls are spaced sufficiently wide apart to receive the swivel 22 of the handle assembly 12 there between. In particular, the first segments are spaced apart to receive the swivel base 50. Second segments 104 of the side walls extend from the first segments 102 and are closer together than the first segments. The second segments 104 are spaced sufficiently apart to closely receive the flexible latches 60 of the swivel 22 between them.

Figure 9:
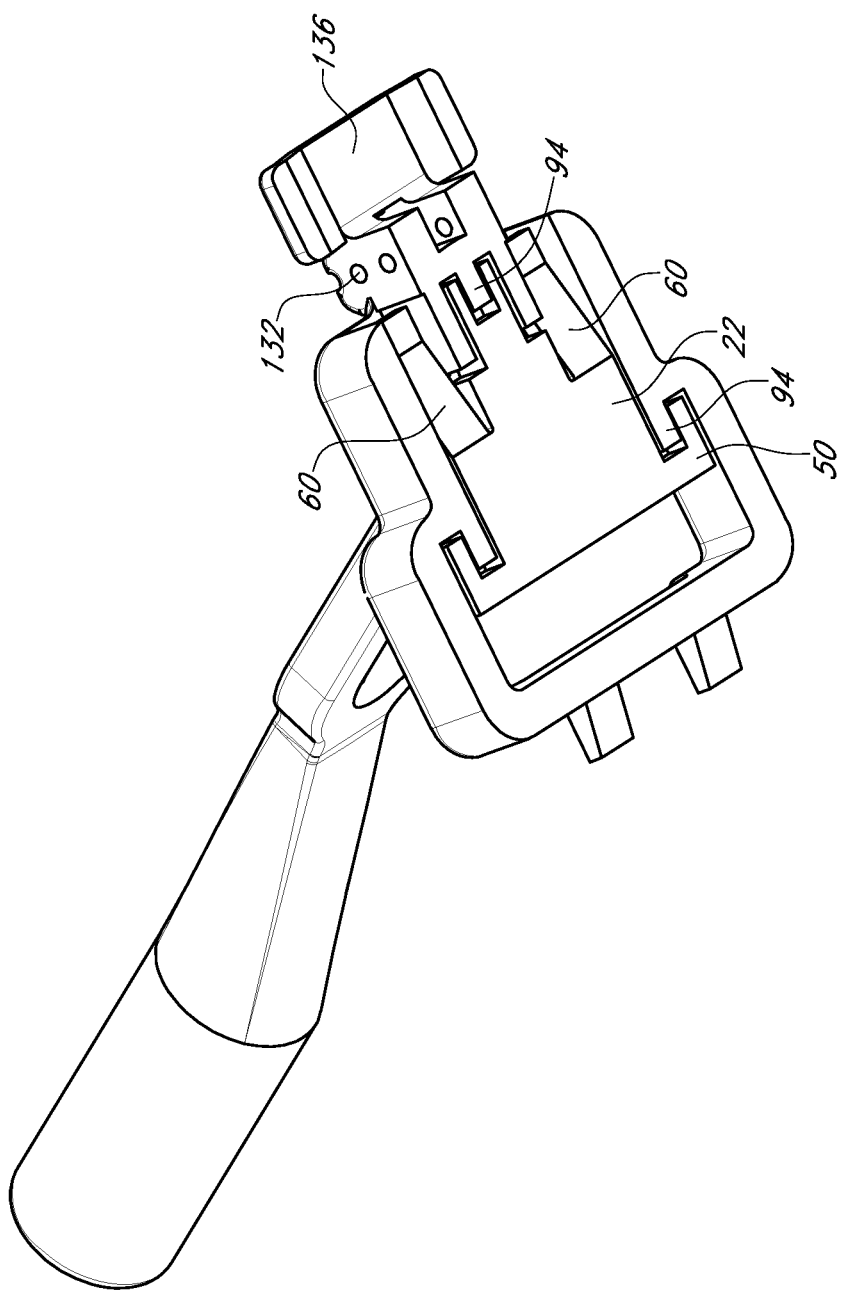
FIG. 9 shows a bottom perspective view of the handle assembly and the valve latch of the heart valve implant holder assembly of FIG. 3 in the assembled state.

The retention tabs 94 of the valve latch 80 mentioned above, extend from the bottom of each side wall second segment 104 in the direction of the back wall 86. The retention tabs 94 are located to support the base 50 of the swivel 22 from the bottom (see FIG. 9). An overhang 98 of each first segment 102 extends into the opening 84 to assist in guiding the base 50 of the swivel 22 into a snap lock position with the valve latch 80 as described further below.

The front wall 90 of the valve latch 80 has a central opening 110 positioned to receive the central bearing 58 of the swivel 22 as well as the distal end 44 of the clevis 24. A lower portion 112 of the central opening 110 has a smaller width to more closely receive the central stub 56 of the swivel 22.

The front wall 90 is further provided with two tunnels 114, each tunnel adjacent a respective side wall 88 of the valve latch 80 and located in the front wall to receive a respective flexible latch 60 of the swivel. On the front side of each tunnel 114 is a recessed portion 116 of the front wall forming a vertical lock wall 118 that the retention wall 68 of the flexible latch can engage against to permit latching of the swivel inside the front wall.

Extending from the front wall 90 between the tunnels 114 is a suture mount 120 formed by two spaced apart walls 122 and a connecting wall 124. A top 126 of each of the spaced apart walls has a groove 128 for supporting a suture across an opening 130 between the walls. The opening 130 is wide enough to receive a cutting instrument (not shown). Multiple holes 132 are located in each wall 122 to permit tying off sutures. The connecting wall 124 has the retaining tab 94 extending into the central opening 110 of the front wall 90 to help support the central stub 56 of the swivel 22 from the bottom at the swivel recess 72. Extending forward from the top of the suture mount 120 is a suture guard 136, the purpose of which will be described below.

FIGS. 4A and 4B show the handle assembly in its final snapped-in position with the valve latch 80. Before reaching this final position, however, the handle assembly 12 is dropped into the opening 84 between the side walls 88 of the valve latch. In particular, the base 50 of the swivel 22 (FIG. 7A) fits between the first segments 102 of the sidewalls 88, where the opening 84 is at its widest. The swivel 22 is then slid forward to snap into place with the valve latch 80. In particular, the flexible latches 60 of the swivel 22 snap against the lock walls 118 (FIG. 8B) of the valve latch. At that point, the valve latch 80 can be articulated from the control on the handle. It will also be appreciated that the swivel 22 is also supported by the valve latch 80 at three locations where the tabs 94 of the valve latch engage respective recesses 72 (FIGS. 7B and 9) of the swivel 22.

With reference again to FIGS. 3-5, the valve holder 14 includes a body 152, a rotor 154, and a guide 156. As described further below, the valve holder 14 can be activated or deployed by the activator dial 16 to reduce or eliminate the occurrence of suture looping over the commissures of the prosthetic heart valve during the surgical procedure.

Figure 10A:
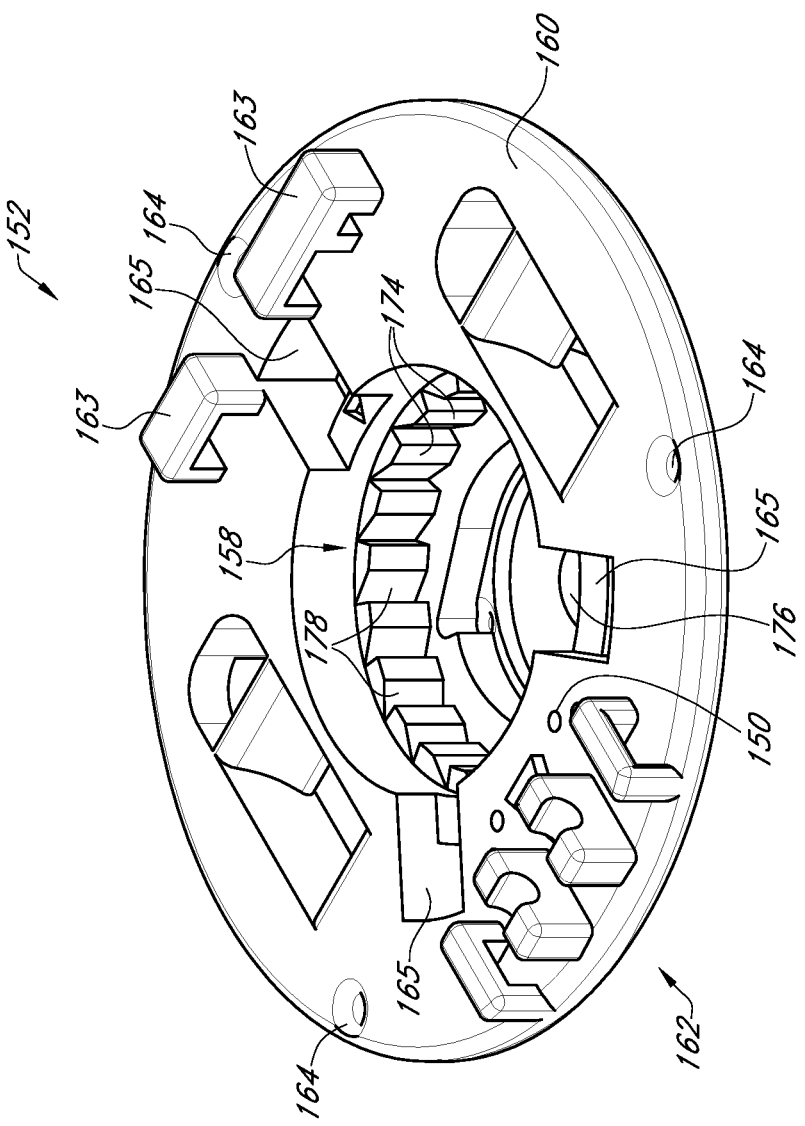
FIG. 10A shows a top perspective view of a valve holder body of the heart valve implant holder assembly of FIG. 3.
Figure 10B:
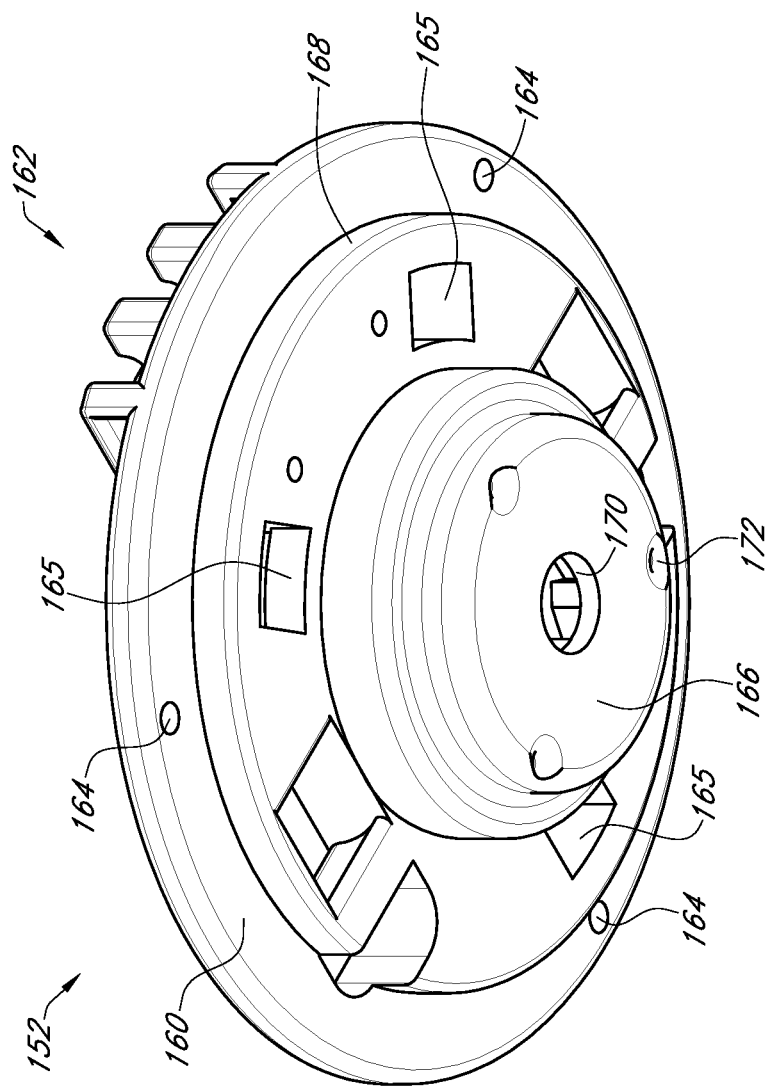
FIG. 10B shows a bottom perspective view of the valve holder body of the heart valve implant holder assembly of FIG. 3.

With reference to FIGS. 10A and 10B, the valve holder body 152 has a round or circular platform 160 with a suture mount 162 located at a periphery of the platform 160 and guides 163 at an opposite side of the platform 160. The body 152 has three suture holes 164 through the platform 160 for routing sutures that are used to deploy the prosthetic valve in a delivery position where the commissure posts are angled radially inwards toward the center of the valve to reduce or eliminate looping. Suturing the prosthetic heart valve to the valve holder to enable this feature is described in detail in U.S. Patent Application Publication No. 2018/0116795, the contents of which are incorporated herein by reference in their entirety.

In the valve holder body 152, an opening 158 is provided for receiving the rotor 154 therein. An abutting surface 176 serves as a stop for the rotor 154. The opening 158 extends to a bottom portion 166 of the body 152 that is circular-shaped and has a smaller outer diameter than an upper central hub 168 to provide clearance for a connected prosthetic valve. A through hole or bore 170 is formed in the bottom portion 166 for coupling the rotor 154 to the body 152 as explained below. The bottom portion 166 additionally includes through holes or bores 172 for routing the sutures from the tips of the commissure posts to the opening 158 for attachment to the rotor 154. Three channels 165 also run along the bore 164 to receive the guide 156.

Figure 11A:
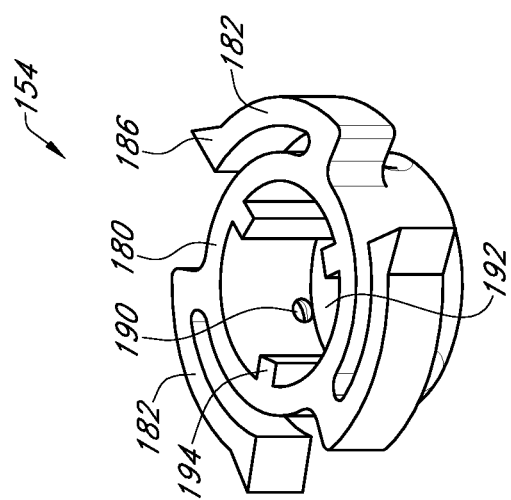
FIG. 11A shows a top perspective view of a valve holder rotor of the heart valve implant holder assembly of FIG. 3.
Figure 11B:
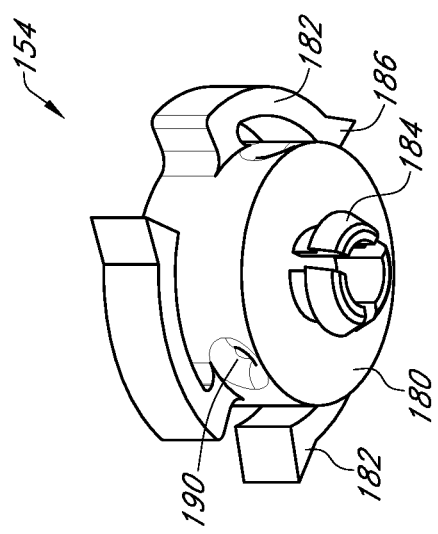
FIG. 11B shows a bottom perspective view of the valve holder rotor of the heart valve implant holder assembly of FIG. 3.

With reference to FIGS. 11A and 11B, the rotor 154 is configured to be positioned inside of the opening 158 of the valve holder body 152 and is rotatable with respect to the body 152. The rotor 154 is connectable to the sutures for adjusting the prosthetic valve to the delivery position using the activator dial 16. The rotor 154 includes a central portion 180 with a longitudinal axis and a plurality of outwardly extending flexible arms 182. The flexible arms 182 are resilient such that the arms can be deflected inwards towards the central portion 180 and then released, causing the arms 182 to spring back into a relaxed shape when no longer deflected.

The rotor 154 includes a coupling mount 184 on the central portion 180 to rotatably couple to the hole 170 in the bottom portion 166 of the body 152. When coupled, the connection between the coupling mount 184 and the hole 170 permits rotation, but restricts translational movement of the rotor 154 relative to the body 152. The coupling mount 184 is depicted as a protrusion that extends to a position below the body 152, and may be snap fit into hole 170.

End portions of the arms 182 have an engagement portion 186 in the form of teeth or pawls to engage a corresponding engagement portion 174 of an inner surface of the opening 158 (FIG. 10A), in the form of a plurality of notches or grooves. The teeth 186 of the rotor 154 engage the notches 178 of the body 152 to provide a one-way ratcheting mechanism that allows the rotor 154 to rotate in one direction relative to the body 152 (e.g., clockwise), but that prevents the rotor 154 from moving in a counter or opposite direction (e.g., counter-clockwise).

The rotor 154 additionally includes one or more holes 190 projecting through a sidewall of the rotor 154 and into a central opening 192. The holes 190 provide attachment points for connecting end regions of the sutures to the rotor 154. When the sutures are connected to the rotor 154, rotation of the rotor 154 will create tension in the suture lines and further cause the sutures to be pulled in the direction of the moving rotor 154. Because the sutures are connected to the commissure posts of the prosthetic valve, this pulling force activates or deploys the valve holder 14 to adjust the prosthetic value to a collapsed or delivery position by transferring the force onto the commissure posts of the prosthetic valve. The commissure posts are thereby radially urged inwards toward a center of the prosthetic valve. The central opening 192 of the rotor also defines alignment keys 194 in the shape of longitudinally extending protrusions to mate with alignment keyways 197 of the activator dial 16. (see FIG. 3)

Figure 12:
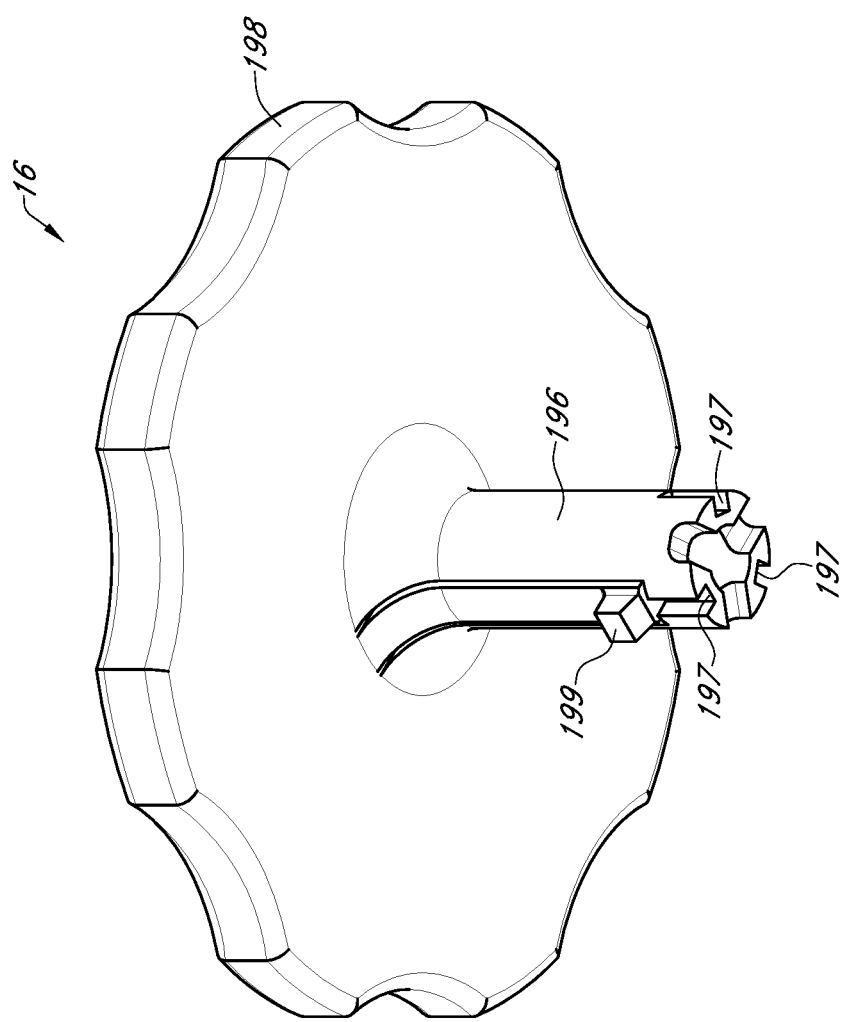
FIG. 12 shows a perspective view of an activator dial of the heart valve implant holder assembly of FIG. 3.

With reference to FIG. 12, the activator dial 16 has keyways 197 that receive the keys 194 of the rotor 154 to rotate the rotor and adjust the valve holder 14 to the deployed configuration. The activator dial 16 can be assembled with the valve holder 14 prior to use in a surgical procedure in an operating room. In one embodiment, for example, the activator dial 16 can be preassembled with the valve holder 14 during an assembly process by the manufacturer of the valve holder 14. Such an assembly step prior to use in surgical procedures can be done in order to aid in proper usage of the valve holder 14 and reduce the risk of inadvertent user errors. The dial 16 includes a central shaft 196 having a central axis, and an enlarged gripping portion 198 extending therefrom. The central shaft 196 is sized and configured to be received in the central opening 192 of the rotor 154.

Figure 13A:
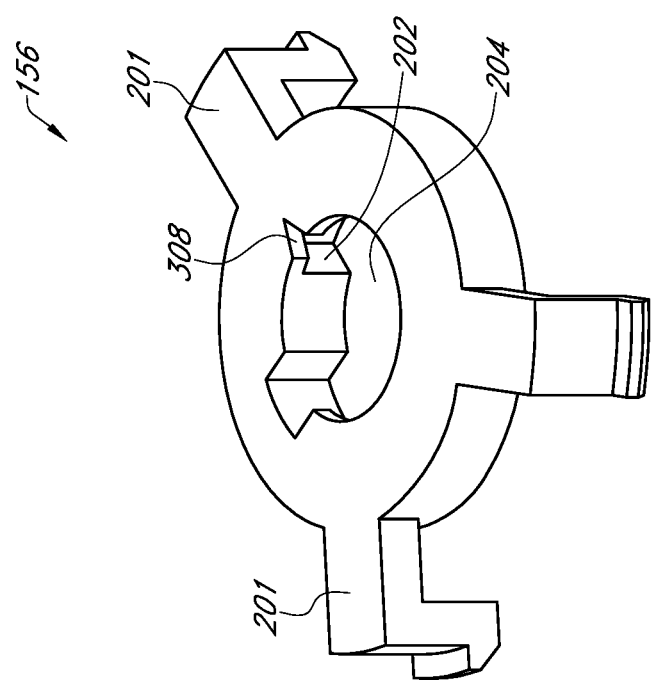
FIG. 13A shows a top perspective view of a valve holder guide of the heart valve implant holder assembly of FIG. 3.
Figure 13B:
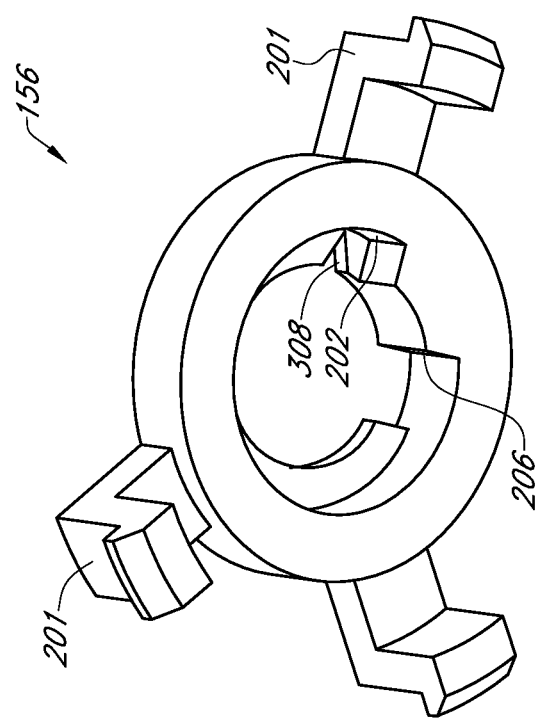
FIG. 13B shows a bottom perspective view of the valve holder guide of the heart valve implant holder assembly of FIG. 3.

With reference to FIGS. 13A and 13B, the guide 156 provides ease of use and prevents misuse of the valve holder 14 during deployment. The guide 156 includes arms 201 and an alignment keyway 202 along an inner periphery of the guide for limiting rotation of the dial 16 and the rotor 154 relative to the valve holder body 152. This is to prevent over-deployment or under-deployment of the valve. The guide 156 is positioned above the rotor 154 such that the dial 16 must pass through a central opening 204 of the guide 156 before the dial 16 can be connected to the rotor 154. The guide has a marker 308 that can be aligned with a flexible key or protrusion 199 of the central shaft 196 of the dial 16. The keyway 202 and a wall 206 of the guide 156 also provide alignment for removal of the activator dial 16 via the key 199. The key 199 can snap into the keyway 202 from above at the marker 308. Then, the keyway 202 and the wall 206 of the guide 156 act as a stop that limits rotation of the dial 16 and the rotor 154 relative to body 152. Full details of operation of the activator dial 16, the guide 156 and the ratchet (178, 186) are provided in U.S. Patent Application Publication No. 2018/0116795 A1.

Assembly of the valve holder proceeds as follows. With reference to FIGS. 3 and 14, the rotor 154 is received in the body 152. Next, the guide 156 is coupled to the body 152 in position over the rotor 154. In particular, the arms 201 of the guide 156 are inserted into the channels 165 of the body 152. Next, one or more sutures (not shown) are used to connect the valve holder 14 to the prosthetic valve, as further described in U.S. Patent Application No. 2018/0116795 A1. The suture or sutures are placed over the suture mount 162 of the body 152 to provide a single access point to release the valve holder from the valve.

Next, the valve latch 80 is secured to the valve holder body 152 by inserting the retention teeth 95 of the valve latch 80 into the guides 160 of the valve holder body 152. A release suture 228 is placed across the suture block 120 of the valve latch 80, through suture holes 150 of the holder body 152, and tied off as needed to secure the valve latch to the body 152.

When the valve latch 80 and the valve holder body 152 are secured together, the suture guard 136 of the valve latch 80 provides an additional safety feature against inadvertent or premature release of the prosthetic valve from the valve holder 14. When the valve latch 80 is coupled to the holder 14, the suture guard 136 is aligned with the suture mount 162 of the body 152, and is positioned over and covers the suture mount 162, thereby preventing or reducing inadvertent or unintended cutting or breaking of the sutures connecting the holder 14 to the valve. When the valve latch 80 is removed, the suture mount 162 is revealed and the suture or sutures connecting the valve holder 14 to the valve can then be cut or untied to release the valve.

The handle assembly 12 is attached to the valve latch 80 as described above. Preferably, this is done after determining the proper size of the prosthetic valve to be used in the procedure.

Prosthetic heart valves come in many sizes and it is important for the surgeon to select the size that best fits the native valve annulus. A tray (not shown) of sizer heads may be provided for this purpose. With reference to FIGS. 15-18, the sizer head 18 has a barrel 210 and a sizer lip 212. The lip 212 is formed by a rim 214 around the top of the sizer head. A gap 216 in the rim provides space for the handle. For a tray of sizer heads, several sizer heads with different barrel sizes are provided from, for example, 23 mm up to 40 mm. In selecting the correct sizer head 18, the surgeon selects the one where the barrel 210 comfortably fits in the native valve annulus and the lip 212 is seated on top of the annulus. The dimensions of the sizer barrel 210 will then match the correct external diameter of the prosthetic heart valve at the stent structure 3 and the lip 212 will match the diameter of the securing ring 5 (see FIG. 2), giving an accurate reflection of the prosthetic fit.

The top of the sizer head 18 has a recess 222 inside the rim 214 and a latch 230 that is similar to the valve latch 80 of the valve holder 14 (FIG. 8A), except in this case the latch 230 may be molded together with the sizer head 18. Features of the valve latch 80 that are not needed for the sizer head latch 230 can be removed, such as the guard 136, the suture mount 120 and the retention teeth 95 of the valve latch 80. The remaining parts of the valve latch of FIG. 8A are similar to the parts in FIGS. 15-18 and are marked with the same reference numbers. Notably, the handle assembly 12 used for the valve holder implant assembly in FIGS. 3-5 may be used with each sizer head of the tray of sizer heads in FIGS. 15-18. Accordingly, the latch 230 on the sizer head should be similar to the valve latch 80 of FIGS. 8A and 8B. One difference, however, is that wherein the valve latch in FIGS. 8A and 8B has a vertical lock wall 118 that the latch wall 68 of the flexible latch 60 engages, the latch 230 of the sizer head has an angled release ramp 232 (see FIG. 18). In this way, the sizer heads reversibly attach to the distal end of the handle by engaging features of the swivel with features of the latch of the sizer head.

Figure 18:
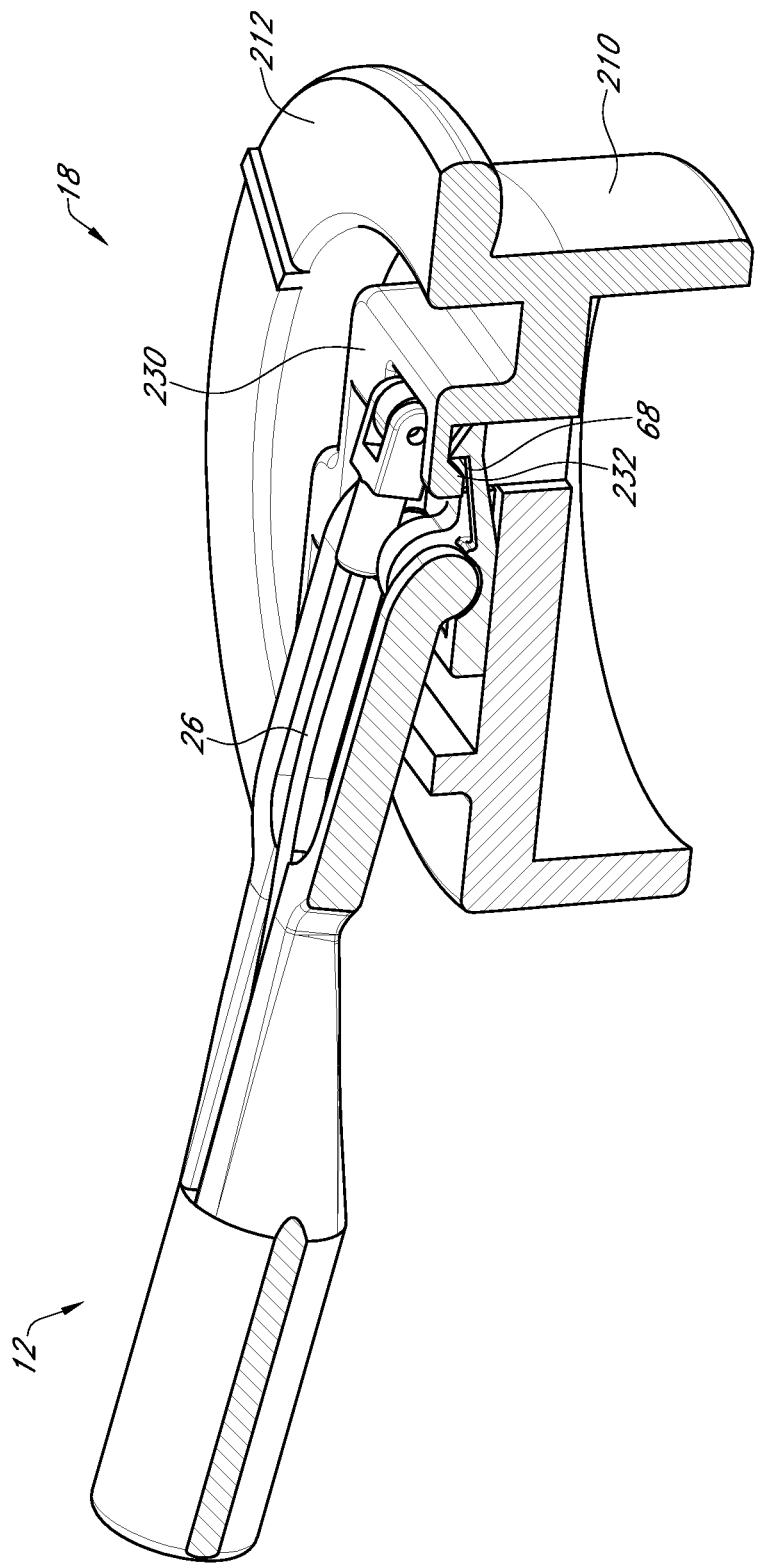
FIG. 18 shows a cross-sectional view of the sizer head of FIG. 16 and the handle attachment of the heart valve implant holder assembly of FIG. 3 in the assembled state.

To attach the handle assembly 12 to a sizer head 18, the swivel 22 on the tip of the handle is initially placed down into the corresponding recess in the top of the sizer head (FIG. 16). Pushing the handle forward into the sizer head (FIG. 17) snaps the swivel into the sizer head. At that point, the sizer head can be articulated from the control on the handle. To remove the sizer head, the handle is pulled back in the opposite direction. The sizer heads reversibly attach to the swivel on the handle because the release ramp 232 will hold the swivel in the sizer head until sufficient force is applied to the handle to deflect the latch of the swivel past the release ramp 232 (FIG. 18). The amount of force needed to release the sizer heads from the handle tip can be optimized by changing the angle of the release ramp.

During use, the surgeon selects a first sizer head to try. The nurse then attaches that sizer head to the handle tip. The handle is tiltable to permit low profile insertion as shown in FIG. 18, but the sizer head may be tilted to a different angle relative to the handle to optimize access into and at the native valve annulus. If the surgeon desires to try a different size, the nurse removes the first sizer head and subsequently attaches the next head using the same procedure. This process is repeated until the surgeon had determined the correct size. Sizer heads can easily be attached and detached, thereby allowing the surgeon to try a variety of different sizer heads until the correct size is determined.

Once the surgeon determines the correct size, a prosthetic valve package is opened and a valve and valve holder of the correct size are selected and deployed by the activator dial 16 as described in U.S. Patent Application Publication 2018/0116795. With reference again to FIG. 3, the activator dial 16 is inserted into the central opening of the guide 156, and connected to the rotor 154. The activator dial 16 is rotated about ¾ turn to fold the commissures to prevent suture looping, and is then removed from the holder 14. Once the activator dial 16 is removed, the same handle assembly 12 used with the sizer heads can be permanently connected to the valve latch 80 as described above for insertion and implantation of the attached valve into a patient. Once the valve is secured to the annulus, the handle and valve latch can be removed by cutting a single suture 228 (FIG. 14). The swivel 22 and valve latch 80 stay attached to one another when the handle is removed from the valve holder, thereby preventing the risk of any parts falling into the patient. With the suture guard 136 of the valve latch 80 also removed, the sutures connecting the valve holder 14 to the valve at the suture mount 162 are exposed. The valve holder 14 can now be removed from the valve by cutting the sutures at a single cut point.

Accordingly, a valve holder implant assembly is provided that uses the same handle with tilting mechanism for both sizing and valve implantation. This gives the surgeon the option of both sizing and implanting the valve through a very minimally sized incision, such as a non-rib spreading thoracotomy.

Figure 19:
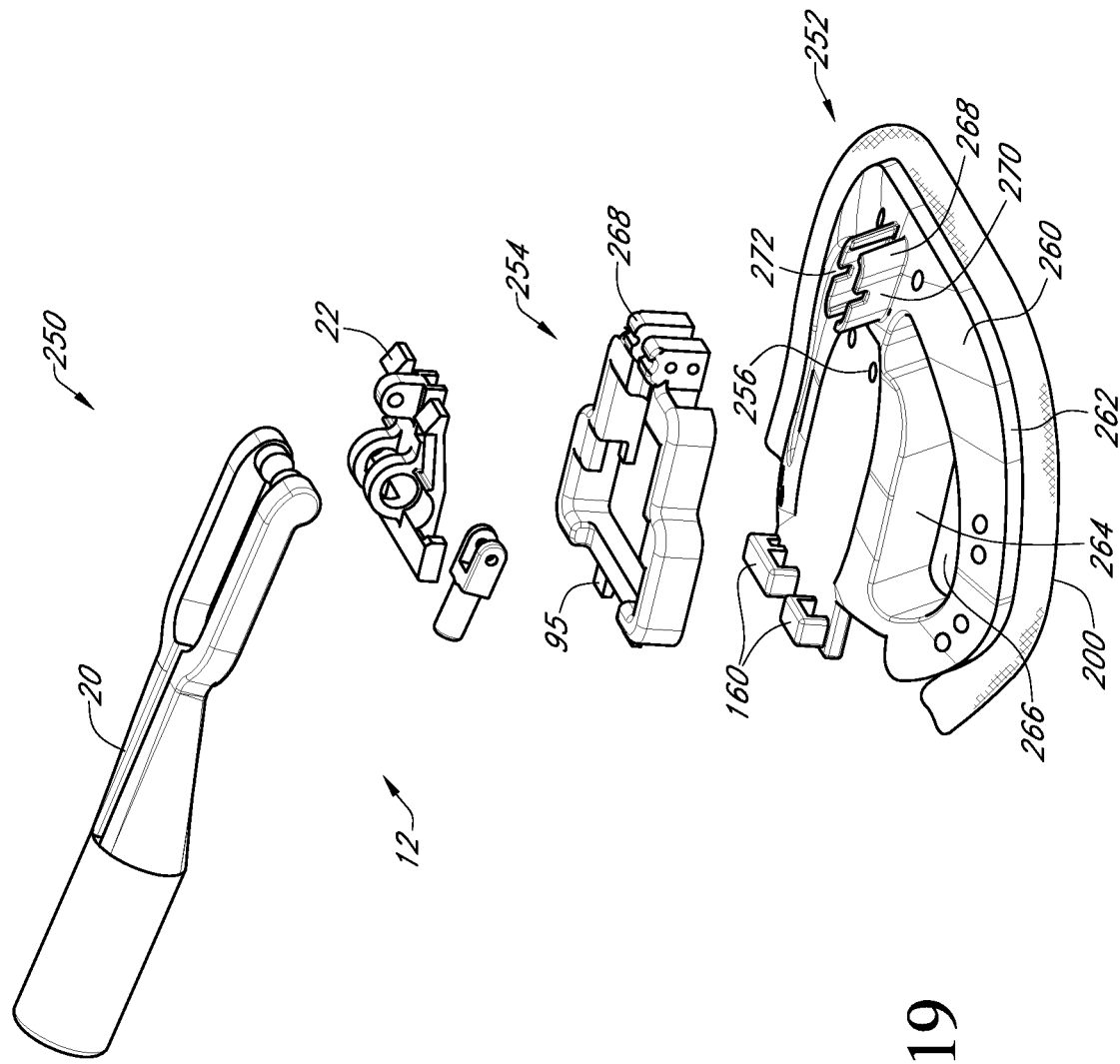
FIG. 19 shows an exploded perspective view of an annuloplasty ring holder assembly according to an embodiment of the invention.

In another embodiment, the articulating handle concept disclosed herein may be used with a holder for an annuloplasty ring, including annuloplasty bands. With reference to FIG. 19, an annuloplasty ring holder assembly 250 includes an annuloplasty ring 200, a handle assembly 12, a ring holder 252 and a ring latch 254. The handle assembly 12 may be similar to that used in the previous embodiment and parts of the handle assembly in FIG. 19 that are similar to the parts of the handle assembly in FIG. 6 are given the same reference numbers.

Annuloplasty ring holders of the present invention may accommodate annuloplasty rings that are open or discontinuous (e.g., C-shaped or otherwise extend at least half way around the valve annulus) or closed or continuous (e.g., D-shaped). The rings may be rigid, flexible, or semi-flexible. The ring holders of the present invention may conform to planar or nonplanar rings, and are adaptable to rings used to repair any of the valves within the heart.

The ring holder 252 is defined by an upper proximal face 260, an outer peripheral edge 262 and a crossbar 264 extending from one side of the peripheral edge to another. The peripheral edge 262 has the same shape in plan view as the annuloplasty ring that it is designed to hold. Between the peripheral edge 262 and the crossbar 264, the ring holder 252 provides a pair of relatively large visibility windows 266 that together occupy a large cross-sectional area within the peripheral edge. The windows 266 allow the surgeon to see distally through the ring holder 252 and the annuloplasty ring to evaluate the condition of the valve annulus as the ring is implanted.

A cutting well 268 projects upward from the proximal face of the ring holder. Walls 270 of the cutting well 268 are located adjacent the peripheral edge 262 and extend upward from the proximal face 260. A notch 272 is provided on an upper edge of each wall 270. The combination of the notches 272 across the two walls 270 provides a convenient bridge across which a connecting suture or sutures for securing the ring holder to the annuloplasty ring are suspended. The walls 270 present one configuration of cutting well that may be utilized, and of course others are contemplated.

The ring holder 252 includes a series of through holes for passage of a suture (not shown) for firmly holding the annuloplasty ring to the ring holder. It should be understood that although through holes are the preferred construction, other configurations that provide passages through the ring holder and/or perform similar functions are contemplated. It will also be appreciated that sutures between the annuloplasty ring and the ring holder can be attached to the ring holder to insure that those sutures are removed together with the ring holder after the annuloplasty ring is delivered to the native valve annulus. Examples of suture routing are described in U.S. Pat. No. 8,152,844, the contents of which are incorporated herein by reference in their entirety.

The ring latch 254 is similar to the valve latch 80 in FIGS. 4 and 14 and similar parts are given similar reference numbers. With reference to FIG. 19, the ring latch 254 is secured to the ring holder 252 by inserting the retention teeth 95 of the ring latch 254 into the guides 160 of the ring holder 252. A release suture (not shown) is placed across the cutting well 268 of the ring latch, through suture holes 256 of the ring holder 252, and tied off as needed to secure the ring latch to the ring holder. A suture guard 136 (FIG. 14) may be provided as an additional safety feature against inadvertent or premature release of the annuloplasty ring from the ring holder 252.

Figure 20:
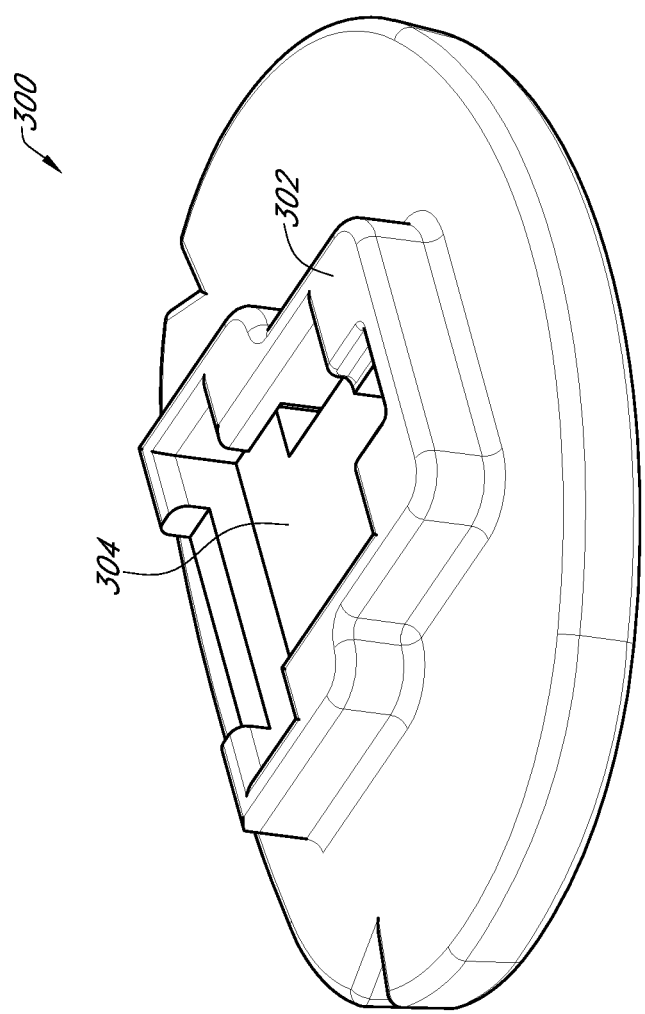
FIG. 20 shows a perspective view of a sizer head according to an embodiment of the invention.

Annuloplasty rings come in many sizes and it is important for the surgeon to select the size that best fits the native valve annulus. A tray (not shown) of sizer heads may be provided for this purpose, including sizes from 24 mm to 40 mm. With reference to FIG. 20, a sizer head 300 has a periphery that is generally shaped the same as an annuloplasty ring. For a tray of sizer heads, several sizer heads with different periphery shapes are provided. In selecting the correct sizer head 300, the surgeon selects the one that matches the valve annulus shape desired. The sizer head is also provided with a latch 302 to receive the handle assembly. The latch 302 may be molded together with the sizer head 300 or attached as a separate part.

It will be appreciated that the same handle assembly used for the ring holder implant assembly in FIG. 19 may be used with the sizer head in FIG. 20. Accordingly, the latch 302 on the sizer head should be similar to the ring latch 254 in FIG. 19. One difference, however, is that wherein the ring latch in FIG. 19 has a vertical lock wall 118 (the same as described in FIG. 8B) that the latch wall 68 engages, the latch 302 of the sizer head 300 has an angled release ramp 232 (the same as described for the sizing head 18 in FIG. 18). In this way, the sizer heads reversibly attach to the distal end of the handle by engaging features of the swivel with features of the latch of the sizer head.

To attach the handle 20 to a sizer head 300, the swivel 22 on the tip of the handle is initially placed down into the corresponding recess 304 in the top of the sizer head. Pushing the handle forward into the sizer head snaps the swivel into the sizer head as in previous embodiments. At that point the sizer head can be articulated from the control on the handle. To remove the sizer, the handle is pulled back in the opposite direction. The sizer heads reversibly attach to the swivel on the handle because the release ramp 232 will hold the swivel in the sizer head until sufficient force is applied to the handle to deflect the latch of the swivel past release ramp.

During use, the surgeon selects a first sizer head size to try. This process is repeated until the surgeon has determined the correct size. Sizer heads can easily be attached and detached, thereby allowing the surgeon to try a variety of different sizes until the correct size is determined. Once the surgeon determines the correct size, an annuloplasty ring of that size with an attached ring holder is selected. The handle assembly 12 can be connected to the ring latch 254 for insertion and implantation of the attached annuloplasty ring into a patient in the same manner as previously described for attaching the handle assembly 12 to the valve latch 80. Once the ring is secured to the annulus, the handle can be removed with the ring latch 254 from the ring holder 252 by cutting the release suture that extends across the cutting well 268. Preferably, the release suture is secured to the ring latch and removed together with the ring latch. The holder 252 is subsequently removed from the annuloplasty ring by cutting the sutures at a single cut point between the notches 272.

Accordingly, a ring holder implant assembly is provided that uses the same handle with tilting mechanism for both sizing and ring implantation. This gives the surgeon the option of both sizing and implanting the ring through a very minimally sized incision, such as a non-rib spreading thoracotomy.

Figure 21A:
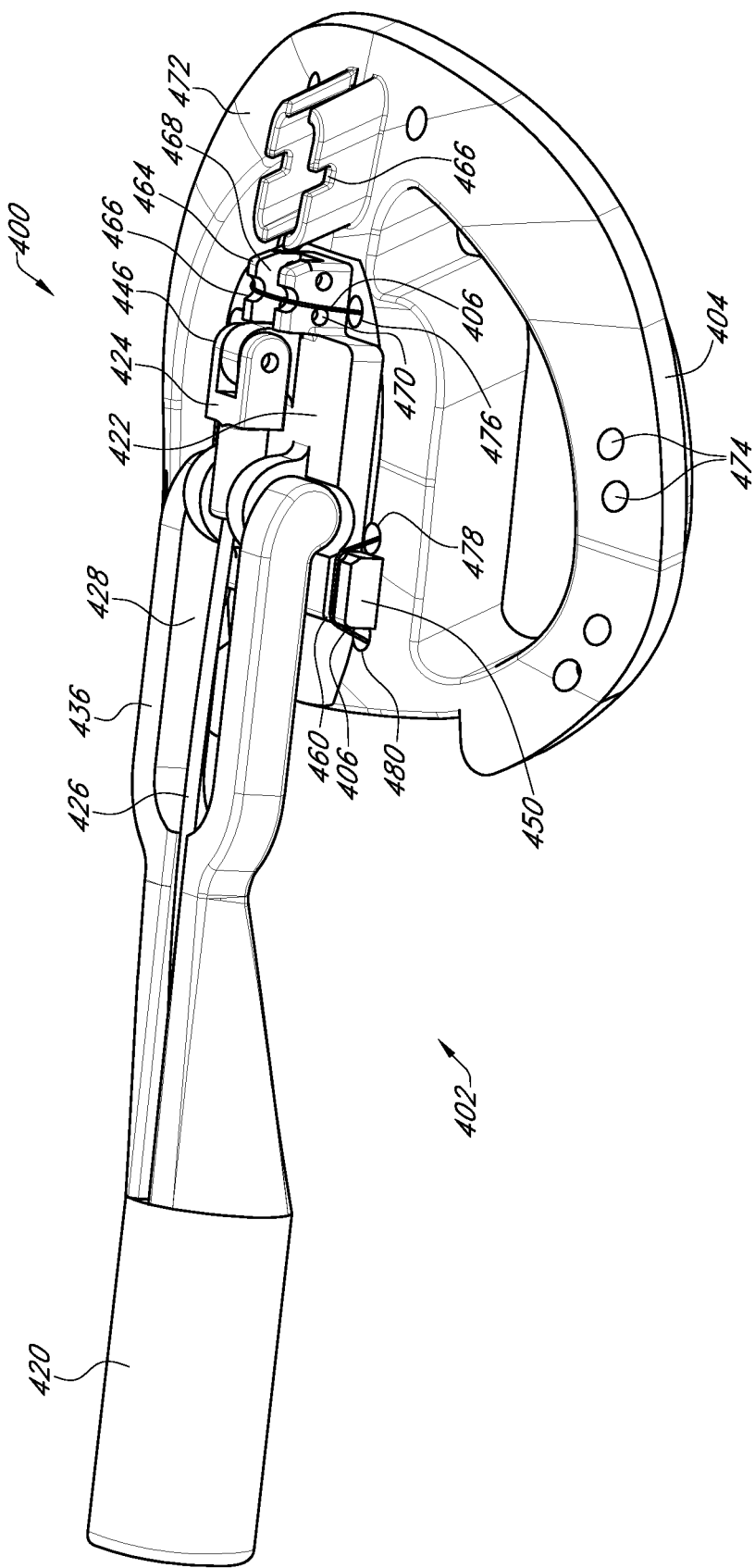
FIG. 21A shows a perspective view of another embodiment of an annuloplasty ring holder assembly in the assembled state with the handle having a first orientation relative to the ring holder.
Figure 21B:
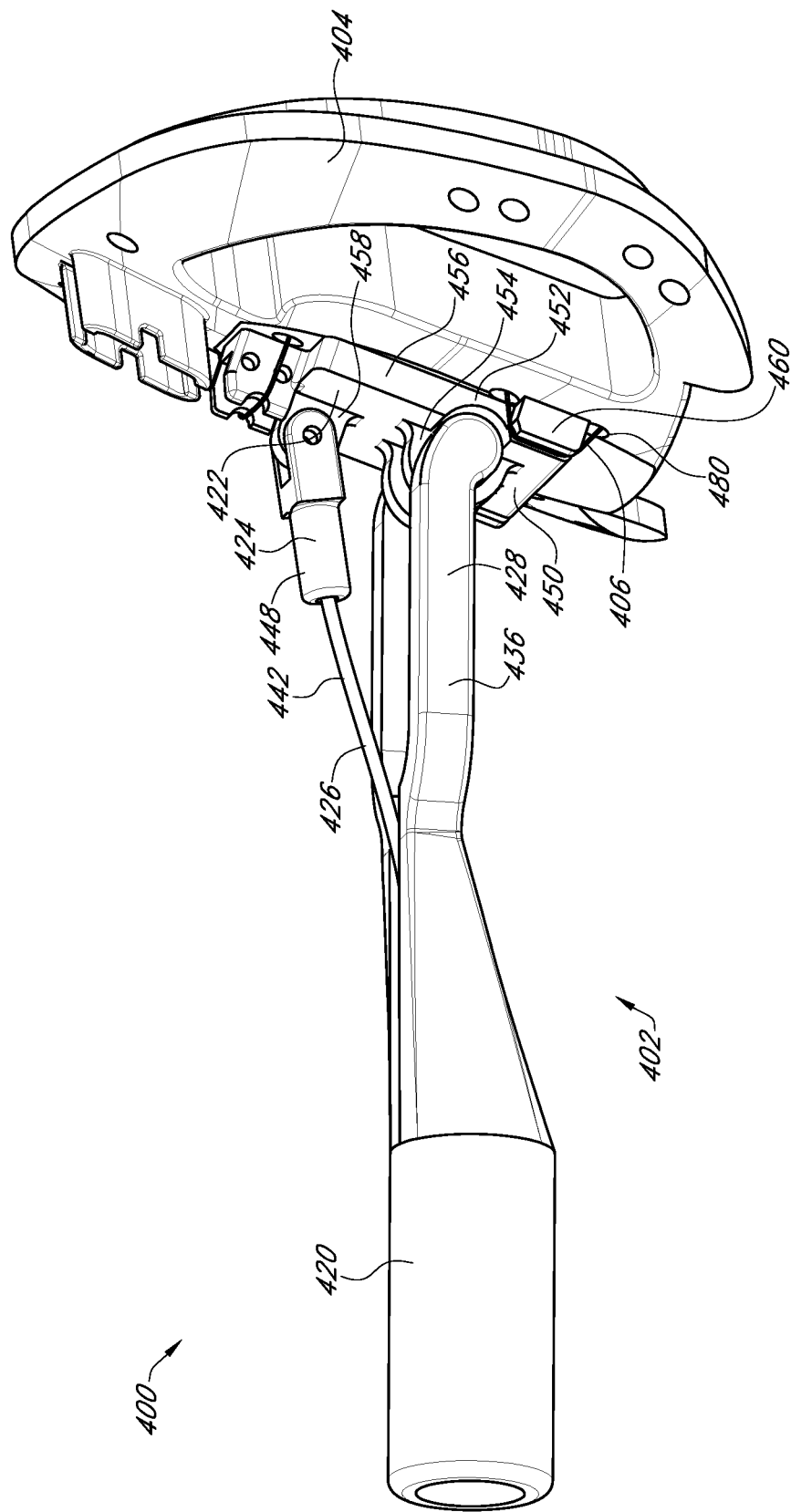
FIG. 21B shows a perspective view of the annuloplasty ring holder assembly of FIG. 21A in the assembled state with the handle having a second orientation relative to the ring holder.

In a further embodiment, FIGS. 21A and 21B depict an annuloplasty ring holder implant assembly 400 having an articulating handle assembly 402 that is pre-attached to a ring holder 404 by a suture or sutures 406. An annuloplasty ring (not shown) can be attached to the bottom of the ring holder 404. The handle assembly 402 includes a handle 420 connected to a rotatable swivel 422 by a clevis 424 and a malleable shaft 426. The swivel 422 rotates at a distal end 428 of the handle and is actuated by the shaft 426 through a toggle or thumb knob (not shown) on a proximal end of the handle.

The distal end 428 of the handle forms a pair of arms 436. The clevis 424 has a proximal shaft 448 to receive and hold a distal end 442 of the shaft 426. A distal end of the clevis forms a pair of arms 446. The arms 436 of the handle and the arms 446 of the clevis are pivotally attached to the swivel 422 to actuate the swivel and move the ring and the ring holder 404 from a low profile orientation (shown in FIG. 21A) to a different orientation (shown in FIG. 21B) that is better suited for securing the annuloplasty ring to the native valve annulus.

The swivel 422 has a base 450, an extension 452 of the base that has connecting ears 454, and a stub 456 that projects from the extension 452 away from the base and supports a central bearing 458. The connecting ears 454 and the central bearing 458 have openings or through holes to facilitate a rotatable connection with the handle arms 436 and the clevis arms 446, respectively.

The base 450 has a top surface with suture grooves 460 formed therein. A bottom surface of the base is flat to match a flat top surface of the ring holder 404. Extending from the stub 456 away from the base 450 is a suture mount formed by two spaced apart walls 464. A top of each of the walls 464 has a groove 466 for supporting a suture 406 across a gap or opening 468 between the walls 464. The opening is wide enough to receive a cutting instrument (not shown). Multiple holes 470 are located in each wall to permit tying of sutures.

The ring holder 404 is similar to the ring holder 252 of FIG. 19 and, in particular, includes a cutting well 472 and suture holes 474 as in the previous embodiment to accommodate a suture that attaches the annuloplasty ring to the ring holder. The handle assembly 402 is attached to the ring holder by knotting the suture 406 around a hole 470 in the wall 464 of the suture mount and passing the suture across the opening 468 between the walls 464. The suture 406 is then fed through holes 476, 478 through the ring holder 404, over the groove 460 on the base 450 of the ring holder 404 and down through a hole 480 in the ring holder 404. The suture is then passed to the other side and threaded in a similar way back to the suture mount to secure the handle assembly to the ring holder.

With reference to FIG. 21A, the ring holder is rotated parallel to the shaft of the handle. In this orientation, the assembly has a very low profile and can readily be inserted through a non-rib spreading thoracotomy. With reference to FIG. 21B, the ring holder is perpendicular to the handle shaft. In this orientation, the implant can be placed on the valve annulus for implant or further adjusted for a more preferred orientation. It will be appreciated that the shaft is malleable to accommodate procedures ranging from full sternotomies to mini-thoracotomies.

After parachuting the annuloplasty ring to the valve annulus, the handle assembly (including the swivel 422) can be released from the ring holder 404 by cutting the suture 406. After sewing the annuloplasty ring to the valve annulus, the ring holder 404 can be released by cutting a second suture extending across cutting well 472. A suture shield as described in other embodiments may also be used in this embodiment. Alternatively, the handle and holder can be removed together by initially cutting the second suture.

In other alternative embodiments, various different features from the different embodiments discussed above can also be combined in a single modified ring holder.

For purposes of this description, certain aspects, advantages, and novel features of the embodiments of this disclosure are described herein. The disclosed methods, apparatus, and systems should not be construed as being limiting in any way. Instead, the present disclosure is directed toward all features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially can in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms can vary depending on the particular implementation and are readily discernible by one of ordinary skill in the art.

In view of the many possible embodiments to which the principles of the disclosure can be applied, it should be recognized that the illustrated embodiments are only preferred examples and should not be taken as limiting the scope of the disclosure. Rather, the scope of the disclosure is defined by the following claims.

What is claimed is:

1. An articulating implant holder system for heart valve repair or replacement, comprising:
   an implant configured to be secured to a heart valve annulus;
   an implant holder having a bottom portion and a top portion, the implant secured to the bottom portion of the implant holder;
   an articulating handle assembly comprising a handle and a swivel, the swivel having a latching feature, the handle pivotably secured to the swivel at a first location, a connector pivotably secured to the swivel at a second location different from the first location, and an actuating cable secured between the handle and the connector to move the swivel from a first position relative to the handle to a second position relative to the handle;
   a latch removably secured to the implant holder; and
   a plurality of sizer heads configured to correspond to different sizes of heart valve annuluses, each of the plurality of sizer heads having a latching feature;
   wherein the latching feature of the swivel is configured to removably snap on to the latching feature of each of the plurality of sizer heads; and
   wherein the latching feature of the swivel is configured to permanently snap on to the latch.

2. The articulating implant holder system of claim 1, wherein the latching feature of each of the plurality of sizer heads comprises a ramp that is configured to engage the latching feature of the swivel to secure the articulating handle assembly to the sizer head and to permit removal of the articulating handle assembly from the sizer head.

3. The articulating implant holder system of claim 2, wherein each of the plurality of sizer heads has a recessed portion to receive the latching feature of the swivel from the top before the latching feature engages the ramp.

4. The articulating implant holder system of claim 1, wherein the implant is a heart valve prosthesis and each of the plurality of sizer heads has a cylinder-like portion extending down from a top portion.

5. The articulating implant holder system of claim 1, wherein each sizer head of the plurality of sizer heads is a monolithic piece.

6. The articulating implant holder system of claim 1, wherein the latch is secured to the top portion of the implant holder by a release suture that is accessible to cutting from above by a surgeon.

7. The articulating implant holder system of claim 6, wherein the latch is further secured by a retention tab located in a retention opening of the implant holder.

8. The articulating implant holder system of claim 1, wherein the latch has a recessed portion and the swivel is configured to enter the recessed portion from the top and is then slidable to a side to permanently snap the latching feature of the swivel on to the latch.

9. The articulating implant holder system of claim 8, wherein the latching feature of the swivel comprises two flexible arms extending away from a base of the swivel, the base of the swivel is supported by the latch when assembled together.

10. The articulating implant holder system of claim 9, wherein a free end of each of the two flexible arms comprises a wall to engage corresponding walls of the latch to prevent the swivel from being removed from the latch.

11. The articulating implant holder system of claim 1, wherein the implant is a heart valve prosthesis and the implant holder further comprises a rotor secured to the heart valve by sutures to move leaflets of the heart valve from a first position where the leaflets of the heart valve are apart to a second position where the leaflets are closer together.

12. The articulating implant holder system of claim 11, further comprising an activator to engage and turn the rotor from the first position to the second position.

13. The articulating implant holder system of claim 12, wherein the latch has a through opening to permit the activator to pass there through to engage the rotor.

14. The articulating implant holder system of claim 1, wherein the implant is an annuloplasty ring.

15. An articulating implant holder system for heart valve repair, comprising:
- an annuloplasty ring configured to be secured to a heart valve annulus;
- an implant holder having a bottom portion and a top portion, the annuloplasty ring secured to the bottom portion of the implant holder;
- an articulating handle assembly comprising a handle and a swivel, the swivel having a latching feature, the handle pivotably secured to the swivel at a first location, a connector pivotably secured to the swivel at a second location different from the first location, and an actuating cable secured between the handle and the connector to move the swivel from a first position relative to the handle to a second position relative to the handle; and
- a latch removably secured to the implant holder;
- wherein the latch is secured to the top portion of the implant holder by a release suture that is accessible to cutting from above by a surgeon; and
- wherein the latching feature of the swivel is configured to permanently snap on to the latch.

16. The articulating implant holder system of claim 15, wherein the latch is further secured by a retention tab located in a retention opening of the implant holder.

17. The articulating implant holder system of claim 15, wherein the latch has a recessed portion and the swivel is configured to enter the recessed portion from the top and is then slidable to a side to permanently snap the latching feature of the swivel on to the latch.

18. The articulating implant holder system of claim 15, wherein the latching feature of the swivel comprises two flexible arms extending away from a base of the swivel, the base of the swivel is supported by the latch when assembled together.

19. The articulating implant holder system of claim 18, wherein a free end of each of the two flexible arms comprises a wall to engage corresponding walls of the latch to prevent the swivel from being removed from the latch.

20. An articulating implant holder system for heart valve repair, comprising:
- an annuloplasty ring configured to be secured to a heart valve annulus;
- an implant holder having a bottom portion and a top portion, the annuloplasty ring secured to the bottom portion of the implant holder; and
- an articulating handle assembly comprising a handle and a swivel, the swivel having a latching feature, the handle pivotably secured to the swivel at a first location, a connector pivotably secured to the swivel at a second location different from the first location, and an actuating cable secured between the handle and the connector to move the swivel from a first position relative to the handle to a second position relative to the handle;
- wherein the articulating handle assembly is mounted on the top portion of the implant holder and is secured by a suture, the suture threaded across a suture mount of the swivel that forms a single cutting point gap, down through the implant holder, and back up through the implant holder to a base of the swivel opposite the suture mount to secure the swivel to the implant holder and to permit release of the articulating handle assembly from the implant holder at a single cutting point at the suture mount.

* * * * *